United States Patent [19]
Buhler et al.

[11] Patent Number: 6,015,383
[45] Date of Patent: Jan. 18, 2000

[54] APPARATUS AND METHOD FOR ACOUSTIC ANALYSIS OF BONE

[75] Inventors: Joe P. Buhler, Portland; David Butt, Beaverton; Jeffrey H. Goll, Lake Oswego; Neldon C. Wagner, Aloha; Hartwell H. Whitney, Portland, all of Oreg.

[73] Assignee: Metra Biosystems, Inc., Mountain View, Calif.

[21] Appl. No.: 08/942,233

[22] Filed: Oct. 1, 1997

Related U.S. Application Data

[60] Division of application No. 08/615,643, Mar. 13, 1996, Pat. No. 5,720,290, which is a continuation-in-part of application No. 08/404,813, Mar. 13, 1995, Pat. No. 5,592,943, which is a continuation-in-part of application No. 08/043,870, Apr. 7, 1993, Pat. No. 5,396,891.

[51] Int. Cl.[7] ...................................................... A61B 8/00
[52] U.S. Cl. ........................... 600/437; 600/442; 600/449
[58] Field of Search .................................... 600/437, 439, 600/442, 443, 449, 459

[56] References Cited

U.S. PATENT DOCUMENTS

| 4,941,474 | 7/1990 | Pratt, Jr. ................................... 600/442 |
| 5,396,891 | 3/1995 | Whitney et al. ......................... 600/449 |
| 5,564,423 | 10/1996 | Mele et al. ............................... 600/449 |
| 5,720,290 | 2/1998 | Buhler et al. ............................ 600/449 |
| 5,785,656 | 7/1998 | Chiabrera et al. ....................... 600/449 |

*Primary Examiner*—Francis J. Jaworski
*Attorney, Agent, or Firm*—Bromberg & Sunstein LLP

[57] ABSTRACT

An improved apparatus and method for providing a measurement of the characteristic behavior of an acoustic wave in a bone of a subject. A preferred embodiment has a first assembly containing mounting means for mounting two transducers in spaced relationship with respect to the bone, and a second, hand-holdable assembly containing a display for displaying an output characterizing the behavior of the acoustic wave in the bone. In other embodiments of the invention, an acoustic signal propagated along a path through the bone is processed to determine the proximity of the path to an edge of the bone.

14 Claims, 21 Drawing Sheets

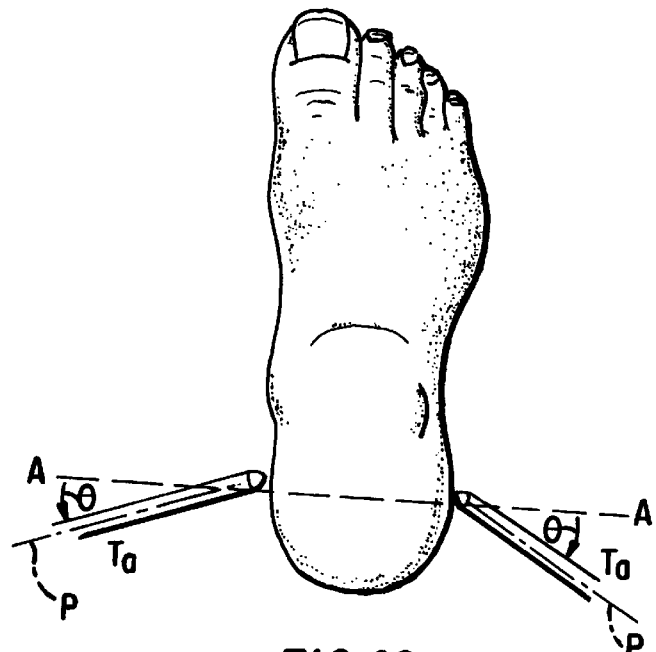
FIG.12
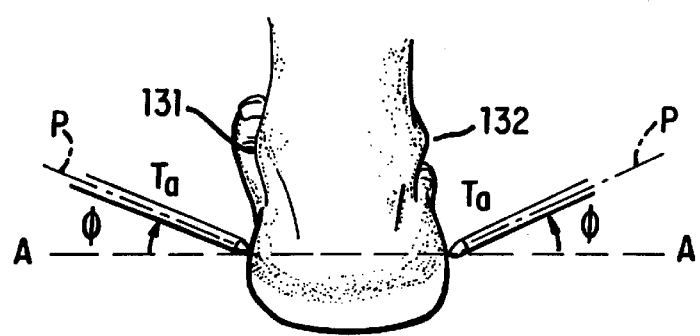
FIG.13
FIG.14

APPARATUS AND METHOD FOR ACOUSTIC ANALYSIS OF BONE

This application is a divisional application of Ser. No. 08/615,643, filed Mar. 13, 1996 and now U.S. Pat. No. 5,720,290, incorporated herein by reference, which is a continuation in part of U.S. application Ser. No. 08/404,813, filed Mar. 13, 1995 now U.S. Pat. No. 5,592,943, which is a continuation in part of U.S. application Ser. No. 08/043,870, filed Apr. 7, 1993, issued on Mar. 14, 1995 as U.S. Pat. No. 5,396,891; these related applications are hereby incorporated herein by reference.

TECHNICAL FIELD

The present invention relates to apparatus and methods for the acoustic analysis of bone, and more particularly to apparatus and methods for accomplishing bone measurement using signal processing techniques.

BACKGROUND ART

The prior art is rich with approaches to measurement of bone characteristics using acoustic and other methods with a view to identifying patients in need of treatment for osteoporosis. Many acoustic techniques utilize a first transducer to provide an acoustic signal, typically at ultrasonic frequencies, to the subject from a first external location and a second transducer at a second external location disposed on the opposite side of the bone of interest to receive the signal transmitted by the first transducer through the bone and intervening soft tissue. (The transducers are typically coupled to the subject through a suitable fluid, such as water.) Under one approach, there is determined the rate of Broadband Ultrasound Attenuation (BUA) in the range of approximately 300 to 700 kHz. The BUA is determined by measurement of the attenuation at a plurality of frequencies and then fitting the measurements to a suitable linear logarithmic-amplitude versus frequency scale. However, as an indicator of osteoporotic bone, BUA does not provide a desirable level of specificity and sensitivity.

SUMMARY OF THE INVENTION

In accordance with a preferred embodiment of the invention, there is provided a system for externally providing a measurement in a vertebrate subject of the characteristic behavior of an acoustic wave in a bone disposed within a body part. This embodiment has first and second transducers and a mounting means for mounting the transducers in spaced relationship with respect to the bone, all of which are contained in a first assembly. Also provided are signal excitation means for causing the first transducer to produce an acoustic waveform that is propagated into the subject and received by the second transducer along a path that includes the bone and characteristic determination means for determining a characteristic of the behavior of the waveform along the path. A display for displaying outputs of the characteristic determination means is contained in a second assembly that is hand-holdable and permits the measurement to be taken while holding the second assembly in one hand of the user. The signal excitation means and the characteristic determination means are collectively contained within the first and second assemblies. In further embodiments, the characteristic determination means includes a signal processor for providing a single measurement that is a function of at least one of spectral or temporal components of a portion, up to the whole amount thereof, of the signal received by the second transducer. The first assembly may be realized as an appliance for removable engagement with the foot of a subject. The appliance has a base having a surface for receiving the sole of a foot having, a longitudinal axis; a cradle rigidly attached to the base, for receiving the subject's foot and ankle, and disposed in a direction transverse to the base; a yoke for supporting the transducers in spaced relationship with respect to the bone; and a member for mounting the yoke in moveable relationship to the base so as to permit joint two-dimensional motion of the transducers over regions of the heel including the calcaneus. The yoke and member constitute the mounting means. The member is a backplate hingedly attached at one end to the base along a first hinge axis generally transverse to the longitudinal axis; and the other end of the backplate is hingedly attached, along a second hinge axis generally parallel to the first hinge axis, to the yoke.

A further embodiment of the invention is the appliance itself, which may include a control module, physically mounted to at least one of the base, cradle, yoke or member. The module has a first set of data ports coupled to the transducers, a second set of data ports for coupling to (i) a signal excitation means for causing a first one of the transducers to produce an acoustic waveform that is propagated into the subject and received by a second one of the transducers along a path that includes the bone and (ii) characteristic determination means for determining a characteristic of the behavior of the waveform along the path. The control module includes a microprocessor for controlling motors for causing displacement of the yoke and therefore the transducers over the calcaneus. The module has a control port over which the microprocessor receives control signals for the motors from a master microprocessor. Preferably, a selected one or both of the transducers employs a vibrating element that is sufficiently small as to cause the transducer, if driven by the signal generator, to produce an acoustical output, into the body part, that is substantially like that of a point source, and each of the transducers employs a resonating element that has a diameter less than 0.5 cm.

In a related embodiment, the invention provides an apparatus for externally determining in a vertebrate subject an index of porosity and non-connectivity of a bone disposed within a body part. The apparatus has first and second transducers; a mounting arrangement for mounting the transducers in spaced relationship with respect to the bone; a signal generator, in communication with the first transducer, for causing the first transducer to produce an acoustic signal, having energy distributed over a frequency range, that is propagated into the subject and received by the second transducer along a first path that includes the bone; and a signal processor, in communication with the second transducer, for providing a single measurement that is a function of at least one of spectral or temporal components of a portion, up to the whole amount thereof, of the signal received by the second transducer. A selected one or both of the transducers employs a vibrating element that is sufficiently small as to cause the selected transducer, if driven by the signal generator, to produce an acoustical output, into the body part, that is substantially like that of a point source; preferably each of the transducers employs a resonating element that has a diameter of less than 1 cm.

A further embodiment provides an apparatus for externally determining in a vertebrate subject proximity of an ultrasonic signal path to an edge of a bone disposed within a body part. The apparatus of this embodiment has first and second transducers; a mounting arrangement for mounting the transducers in spaced relationship with respect to the bone; a signal generator, in commnunication with the first transducer, for causing the first transducer to produce an acoustic signal, having energy distributed over a frequency range, that is propagated into the subject and received by the second transducer along a first path that includes the bone; and a signal processor, in communication with the second transducer, for determining a measure of the relative proportion of high frequency energy in relation to low frequency energy of the signal received by the second transducer. The proportion determined is an indication of the proximity of the first path to an edge of the bone. Preferably, each of the transducers employs a vibrating element that is sufficiently small as to cause each transducer, if driven by the signal generator, to produce an acoustical output, into the body part, that is substantially like that of a point source.

In a related embodiment there is provided a method for externally determining in a vertebrate subject proximity of an ultrasonic signal path to an edge of a bone disposed within a body part. The method includes providing first and second transducers; mounting the transducers in spaced relationship with respect to the bone; utilizing a signal generator, in communication with the first transducer, to cause the first transducer to produce an acoustic signal, having energy distributed over a frequency range, that is propagated into the subject and received by the second transducer along a first path that includes the bone; and processing the signal received by the second transducer so as to determine a measure of the relative proportion of high frequency energy in relation to low frequency energy of the signal received by the second transducer. Again, the proportion is an indication of the proximity of the first path to an edge of the bone. Preferably in step(a) each of the transducers employs a vibrating element that is sufficiently small as to cause each transducer, if driven by the signal generator, to produce an acoustical output, into the body part, that is substantially like that of a point source.

Another embodiment of the invention provides a method for externally determining in a vertebrate subject an index of porosity and non-connectivity of a bone disposed within a body part. The method includes:

(a) providing first and second transducers, wherein a selected one or both of the transducers employs a vibrating element that is sufficiently small as to cause the selected transducer, if driven by the signal generator, to produce an acoustical output, into the body part, that is substantially like that of a point source;

(b) mounting the transducers in spaced relationship with respect to the bone;

(c) utilizing a signal generator, in communication with the first transducer, to cause the first transducer to produce an acoustic signal, having energy distributed over a frequency range, that is propagated into the subject and received by the second transducer along a first path that includes the bone; and (d) processing the signal received by the second transducer so as to provide a single measurement that is a function of at least one of spectral or temporal components of a portion, up to the whole amount thereof, of the signal received by the second transducer.

BRIEF DESCRIPTION OF THE DRAWINGS

The foregoing features of the present invention will be more readily understood by reference to the following detailed description taken with the accompanying drawings, in which:

FIGS. 12, 13, and 14 provide top, rear, and side views respectively of the foot of a subject in relation to a transducer pair $T_T$ and $T_R$ to illustrate orientation of the transducers in connection with a preferred embodiment of the present invention;

DETAILED DESCRIPTION OF SPECIFIC EMBODIMENTS

Contents

Figure 1:
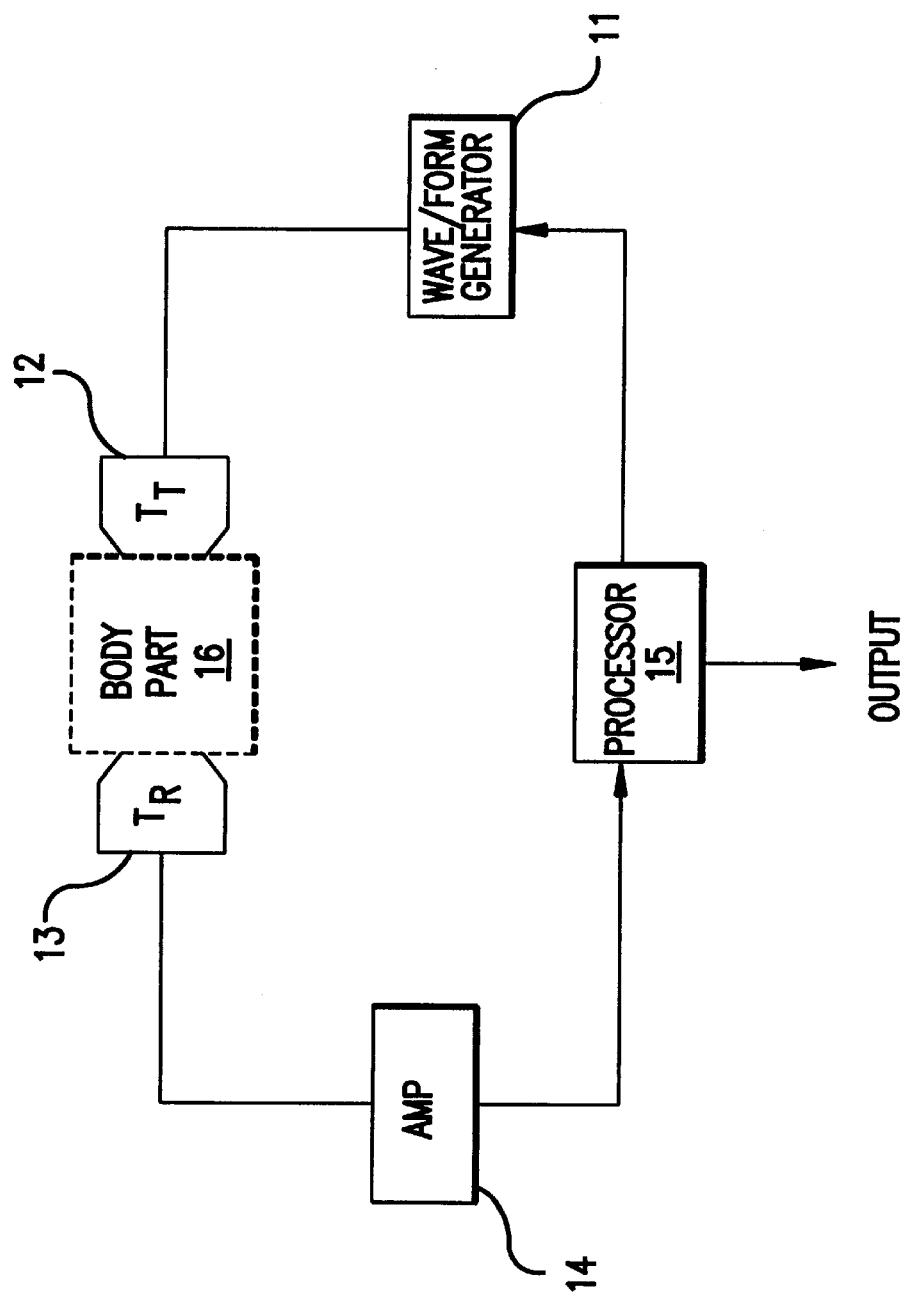
FIG. 1 is a diagram showing in general the components for a system in accordance with a preferred embodiment of the invention.

1. General Arrangements and Signal Generation
2. UBI-2 and Optimized Weighting of Coefficients Generally
3. UBI-3
4. UBI-4
5. UBI-5
6. UBI-6
7. UBI-7
8. UBI-8
9. Composite UBIs
10. Electronics
11. Appliance 1. General Arrangements and Signal Generation FIG. 1 is a diagram showing in general the components for a system in accordance with a preferred embodiment of the invention. In this system, a waveform is generated by waveform generator 11, and delivered to transmitting transducer $T_T$, item 12. The transducer $T_T$ is acoustically coupled to body part 16 of a subject and produces an acoustic wave that is propagated into the body part 16 and in particular into a bone within the body part. The transducer $T_R$, item 13, is also acoustically coupled to the body part 16 and receives a signal resulting from the effects, among other things, of propagation of the acoustic wave through the bone and the body part. The output of the transducer $T_R$ is amplified by amplifier 14 and processed by processor 15. The processor analyzes the output of the transducer $T_R$, and may make a determination reflective of the condition of the bone, and provides an output.

Figure 2:
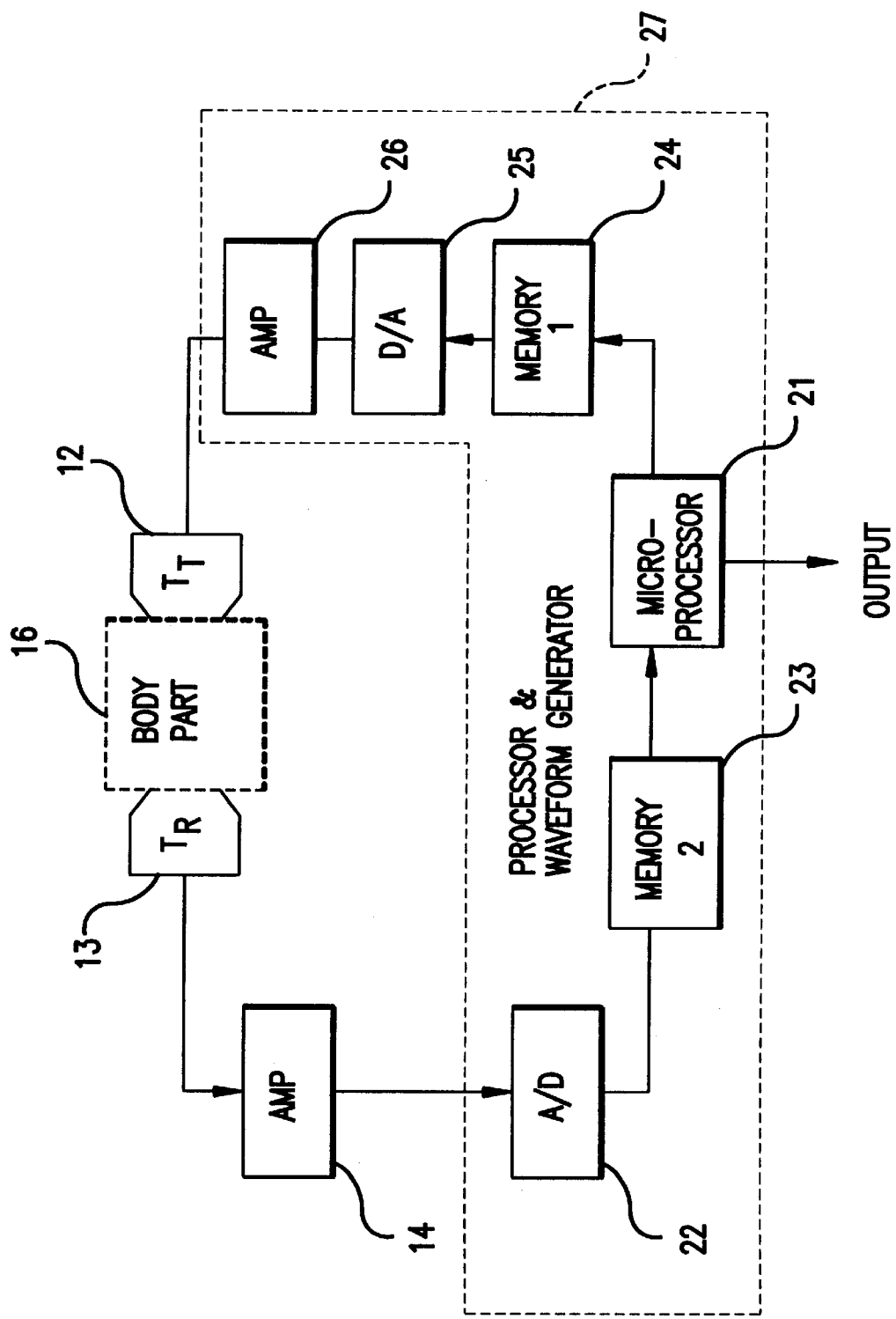
FIG. 2 is a diagram showing an implementation of the system of FIG. 1.

FIG. 2 is a diagram showing an implementation of the system of FIG. 1. The body part may be, for example, the region proximate to the calcaneus. While the elements of FIG. 1 may be implemented in analog components, in a manner known in the art, we have found it convenient to use a digital implementation. Accordingly, the processor 15 and waveform generator 11 may be realized in a single hand-holdable unit 27 including a microprocessor 21 that controls both processing of the output from the transducer $T_R$ and the generation of the waveform used for transducer $T_T$. This waveform is stored in digitized form in memory 1, item 24, and under control of the microprocessor is run through digital-to-analog converter 25 before being provided to amplifier 26 and the transducer $T_T$. Similarly, the output of receiving transducer $T_R$ is fed from amplifier 14 to analog-to-digital converter 22 and this digitized output is stored in memory 2, item 23. The stored output is then processed by the microprocessor 21, which provides a data output indicating the condition of the bone.

In further embodiments of the invention, the embodiments of FIG. 2 (or a wholly or partially analog implementation of FIG. 1) are used to process the stored output of $T_R$ in accordance with any one or more of a variety of procedures to provide a data output indicating the condition of the bone. In accordance with some embodiments, the data output indicating bone condition includes a number, which we call the "Ultrasonic Bone Index" (UBI). Each different procedure we employ can lead to a different UBI, and the various UBI types are identified by a numerical suffix, for example, UBI-2, UBI-3, etc. The procedures for UBI-2 through UBI-8 are described below. In connection with the general signal processing techniques utilized (but not their specific utilization in the context of ultrasonic bone testing), the following references are pertinent: Boualem Boashash, ed., *Time-Frequency Signal Analysis* (Wiley, 1992) (especially pertinent to instantaneous frequency analysis; see especially ch. 2, pages 43–73) and Richard Shiavi, *Introduction to Applied Statistical Signal Analysis* (Irwin, 1991)(especially pertinent to Burg Spectral Estimation; see especially pages 369–373). These texts are hereby incorporated herein by reference.

Our procedures have been developed to take advantage of the fact that relatively nonporous and connective bone, on the one hand, and relatively porous and non-connective bone, on the other hand, respond differently to ultrasound inputs. Although it has been known, for example, that the rate of attenuation with frequency of ultrasound signals in bone may be indicative of bone condition, the prior art measure of such attenuation, namely broadband ultrasound attenuation (BUA), is based on the assumption that the attenuation is log-linear and provides a number associated with the rate of log-linear attenuation. In fact, the embodiment of FIG. 2 can be used to calculate BUA. Using the signal generation arrangement described in the second paragraph below in connection with the FIG. 2 embodiment the discrete Fourier transform of the received signal can be calculated, for example, at five frequencies from 250 kHz to 580 kHz, and these calculations can be the basis for determining the BUA. Alternatively, one can compute the Fast Fourier Transform of a decimated autocorrelation (with white noise added), and to the resulting spectrum over a broad band, say from 300 kHz to 600 kHz, is fitted a straight line, the slope of which is the BUA.

Our investigations have led to the discovery, however, that relatively connective and nonporous bone, on the one hand, and relatively porous and non-connective bone, on the other hand, can be better distinguished by utilizing more information in the ultrasonic signals propagated through bone than is used in arriving at the BUA. We have thus found that the difference in effects between strong and porous bone is not one that can be measured wholly by utilizing the prior art BUA. The procedures outlined below take advantage of these and other observations.

Figure 3A:
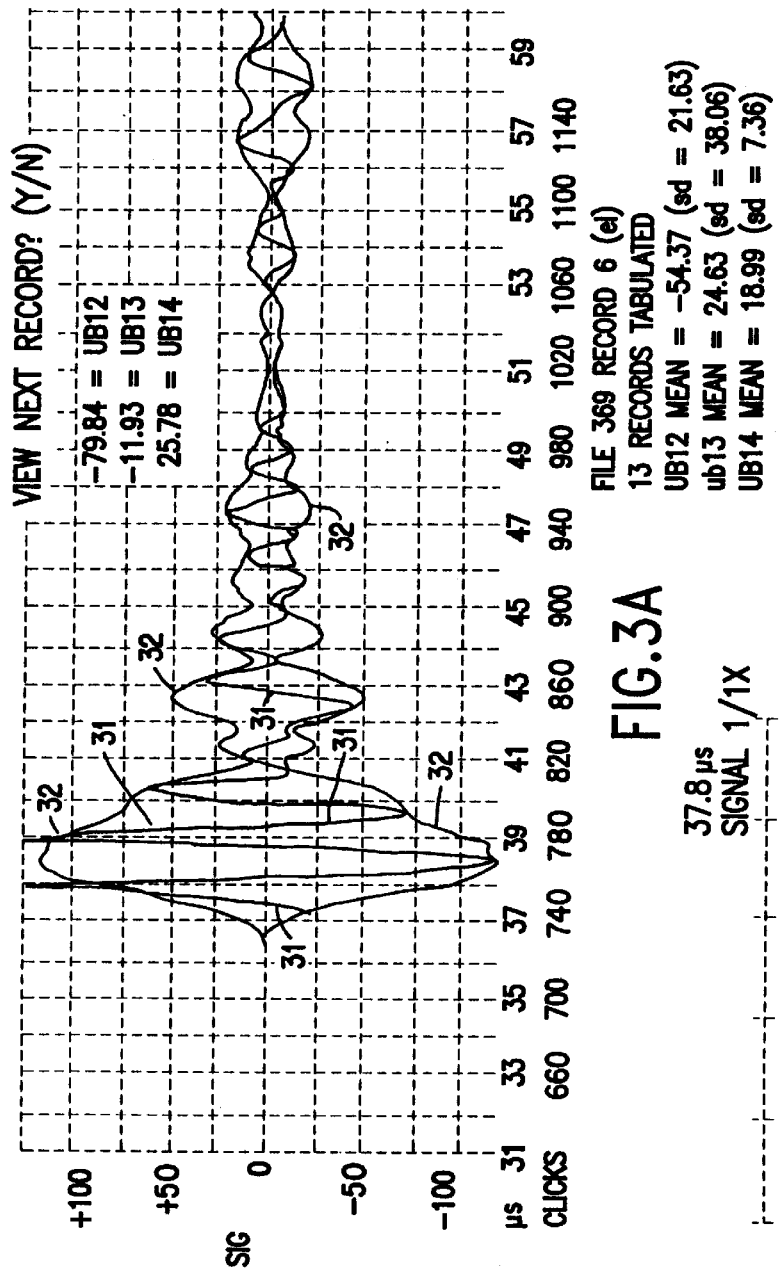
FIG. 3A provides a plot showing the stored output of transducer 13 of FIG. 1 in response to an excitation waveform, generated by the system of FIG. 1 and transmitted from transducer 12 through water only, as well as plots pertinent to calculation of UBIs in accordance with a preferred embodiment of the invention, shown here as controls.
Figure 3B:
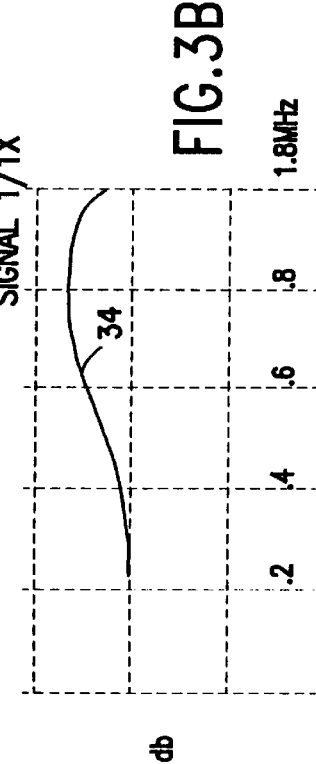
FIG. 3B provides a plot of the Burg spectral estimation function associated with the plots of FIG. 3A.
Figure 4A:
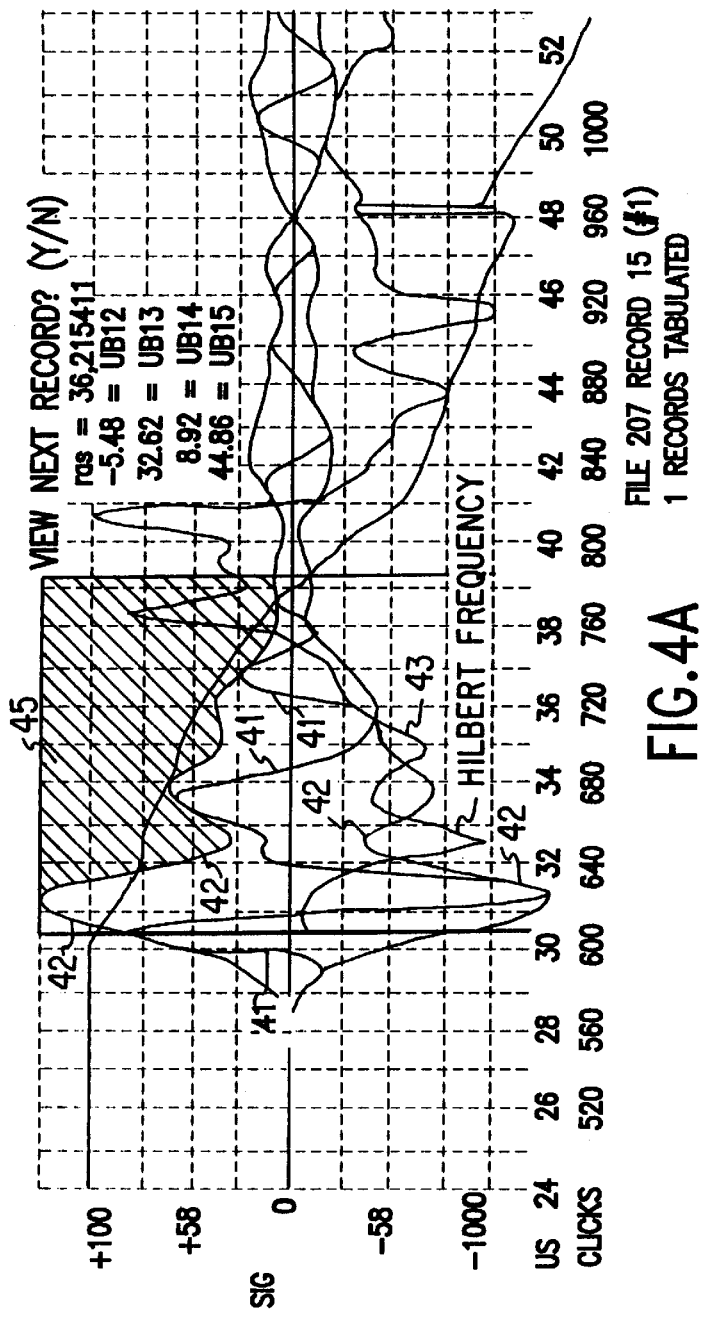
FIG. 4A provides a plot showing the stored output of transducer 13 FIG. 1 in response to an excitation waveform, generated by the system of FIG. 1 and transmitted from transducer 12 through a bone having substantial porosity, as well as plots pertinent to calculation of UBIs in accordance with a preferred embodiment of the invention, FIG. 4B provides a plot of the Burg spectral estimation function associated with the plots of FIG. 4A.
Figure 4B:
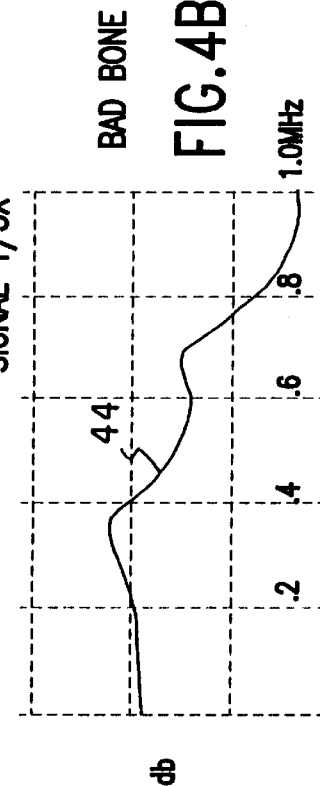

In the examples that follow, $T_T$ is supplied with a short pulse of about 500 nanoseconds duration. In this case the pulse has a sawtooth shape, with a rise time to the peak of about 200 nanoseconds and a decay time of about 300 nanoseconds. The sound output of $T_T$ is a short burst (with some ringing) having a fundamental frequency of about 1 MHz. Because $T_T$ is putting out a transient signal, however, useful components at frequencies within a range from about 200 kHz to 1.5 MHz are present as well. For the purposes of illustration of the nature of the burst, FIG. 3A provides a plot 31 showing the stored output of transducer 13 ($T_R$) of FIG. 1 in response to an excitation waveform, generated by the system of FIG. 1 and transmitted from transducer 12 ($T_T$) through water only. (FIG. 3A also shows the Hilbert envelope 32 of the waveform 31, while FIG. 3B shows the Burg spectral estimation function associated with the waveform 31. These concepts are discussed below.) Also as described in further detail below, the transducers are in this embodiment designed to generate a small-sized excitation area (of the order of 0.3 cm) and to have substantially non-directional characteristics, so that the transmitting transducer 12 behaves substantially like a point source. And the receiving transducer behaves substantially like a point receiver.

The received signal is, of course, influenced not only by the excitation area of the transmitting transducer 12 and the size of the receiver but also by the signal path. Given the physical size of the calcaneus and the speed of ultrasound in bone, it takes approximately 30 $\mu$sec after initiation of the burst for any output to be received by the receiving transducer 13. For example, a duration window of 10 $\mu$sec after this 30 $\mu$sec delay permits analysis of signal due to all signal paths having a length between 4.5 cm and 6.0 cm, assuming a velocity of 1500 m/sec. Analysis of received signal behavior that occurs approximately within this window is advantageously used in accordance with a preferred embodiment of the invention, although other windows are within the scope of the present invention.

2. UBI-2 and Optimized Weighting of Coefficients Generally

In accordance with UBI-2, the stored output of $T_R$ is run through a discrete Fourier transform. A weighted linear sum of the logarithm of resulting frequency components is then computed; this sum is UBI-2. The weights are chosen to minimize differences among successive measurements taken of the same individual and to maximize differences in measurements taken of different individuals, so that the function acts as a discriminant in determining the extent of non-connectivity and porosity of bone. The weights may be selected empirically using manual techniques. They may also be selected using neural net techniques known in the art; see U.S. Pat. No. 5,259,384 for an invention of Kaufman. They also may be determined analytically in accordance with the method described below in the next two paragraphs.

An analytic method for optimization of linear coefficients method is described in this paragraph. Suppose that repeated observations are made on individuals in a population. Thus, in each experiment we measure a vector $v=(v_1, \ldots, v_n)$. (This vector v may, for example, constitute the magnitudes of n frequency components of the received signal; but it may be any other set of measurements associated with an individual, as discussed in further detail below.) We seek the coefficients $a_k$ of a linear combination of these vector components $v_k$, thus:

$$s = \sum_{k=1}^{n} a_k v_k,$$

in such a way that the "score" minimizes the variance attributable to repeated measurements taken of the same individual while at the same time maximizing the range of the score and approximately conforming to our prior notions of how the individual should score. Thus $a_k$ is a "weight" assigned to the k-th variable $v_k$ of the vector v, and we are searching for an optimal weighted linear combination of the variables. In order to specify the method for doing this, we assume that the repeated measurements have been made that lead to vectors v(i,j), which are the results of the j-th measurement on individual i. A weighting vector $a=(a_k)(k=1, \ldots, n)$ leads to a score of the form $$S_a(v(i, j)) = \sum_{k=1}^{n} a_k v(i, j)_k.$$

The mean score on individual i is $S_a(v(i))$ where $$v(i) = \frac{1}{N_i} \sum_{j=1}^{N_i} v(i, j)$$

is the mean of the observations on individual i and $N_i$ observations are made on individual i. The average "within-individual" variance, where there are N individuals, is therefore $$I(a) = \frac{1}{N} \sum_{i=1}^{N} \frac{1}{N_i - 1} \sum_{j=1}^{N_i} (S_a(v(i, j)) - S_a(v(i)))^2.$$

Now let $$v = \frac{1}{N} \sum_{i=1}^{N} v(i)$$

be the average of the observations of all individuals. Then the "between-individuals" population variance is $$P(a) = \frac{1}{N-1} \sum_{i=1}^{N} (S_a(v(i)) - S_a(v))^2$$

We want to find a scoring vector such that the quotient $$\frac{I(a)}{P(a)}$$

is minimized. This "generalized Rayleigh quotient" is a quotient of quadratic forms, and is optimized by choosing a minimal generalized eigenvalue $\lambda$.

where $$Aa=\lambda Ba$$

and where the matrices A and B correspond to the quadratic forms in the usual way:

$$I(a)=a^{tr}Aa, \; P(a)=a^{tr}Ba.$$

The calculation of these generalized eigenvalues can be performed in several ways well known in the art. See for example, J. Stoer and R. Bulirsch, *Introduction to Numerical Analysis* (Springer-Verlag, New York, Second Edition, 1991), page 405, which discusses generalized eigenvalue problems. The upshot is that the coefficients of an optimal linear model built on the data v can be obtained by combining the observed data into the above linear model.

It is possible to incorporate prior subjective scores into this procedure. More precisely, suppose that we believe that individual i should have the score $s_i$. Then we modify the above problem by replacing I(a) by $$I(a) + t\sum_{i=1}^{N}(a_{n+1} + a_{n+2}s_i - S_a(v(i)))^2$$

where t is a parameter that determines how heavily we want to force the computed scores to match our prior beliefs. The resulting problem is identical in form to the prior one, except that there are two new variables $a_{n+1}$ and $a_{n+2}$. If the parameter t is large then this becomes a linear regression problem. If the parameter is small, then we are more interested in minimizing the average variance (as a fraction of the population variance) as above. The method assumes that the scores should depend only linearly on the measured values. We find that experimentation is valuable, both for choosing which observations to consider, and for choosing the parameter t.

It will be appreciated that the weights determined using any of the procedures above are dependent on the precise characteristics of the system employed, including characteristics of the transducers, the waveform input to $T_T$, the circuits and processing associated with the signal from $T_R$, and the data with respect to which the weights are optimized. A sample set of weights for UBI-2 is set forth in Table 1 below.

TABLE 1

| Frequency (MHz) | Program Weights | Simplified Weights | Constrained Weights |
| --- | --- | --- | --- |
| 0.000 | 0.0718 | 0.0 | 0.0 |
| 0.125 | 1.0000 | 1.0 | 1.0 |
| 0.250 | 0.225 | 0.2 | 0.0 |
| 0.375 | −0.406 | −0.4 | −0.4 |
| 0.500 | −0.0767 | 0.0 | 0.0 |
| 0.625 | −0.506 | −0.5 | −0.6 |
| 0.750 | −0.0372 | 0.0 | 0.0 |
| 0.875 | −0.139 | −0.1 | 0.0 |
| 1.000 | −0.0365 | 0.0 | 0.0 |
| 1.125 | −0.0486 | 0.0 | 0.0 |
| 1.250 | 0.0946 | 0.0 | 0.0 |
| 1.375 | −0.00858 | 0.0 | 0.0 |

The data in Table 1 were derived from data collected on 21 subjects. The weights for each frequency component used in UBI-2 appear in columns 2, 3, and 4. In the second column are weights as calculated using the analytical approach discussed above. In the third column are the weights resulting after using only the five largest weights and then rounding to one significant figure. This column produces results that are only slightly degraded from those using the weights in column 2. In column 4 are weights resulting after using only the three largest weights and then modifying them slightly so that they sum to 0. The column produces results that in turn are only slightly degraded from those using the weights in column 3. It is preferred to use weights in this context that sum to 0, so that a change in gain does not produce a change in the resulting UBI-2. Note that the weights in Table 1 are greatest in the regions of 100–200 kHz (positive) and 500–700 kHz (negative).

3. UBI-3

The UBI-3 procedure utilizes the Hilbert envelope of the stored output of $T_R$; the Hilbert envelope provides a measure of the energy content of the received waveform as a function of time. The greater preponderance of low frequency signals in the received waveform associated with healthy bone causes it to have a longer duration than in the received waveform associated with relatively porous bone. Accordingly, in accordance with UBI-3, the Hilbert envelope is examined for energy duration. A relevant time period of the stored output is examined; for this time period, there is determined the fraction of area lying above the plot (of the top half of the envelope) and beneath a fixed value defined by the first peak in the plot. In one embodiment, the relevant period begins 1 microsecond after the first peak in the Hilbert envelope and continues for a total of 8 microseconds. In a further embodiment, UBI-3 is instead the curvature of the envelope over the first few microseconds following the first peak.

FIGS. 3A, 4A, 5A, and 6A are illustrative for the case of transmission through water, relatively porous bone, low-normal bone, and exceptionally healthy bone respectively. Plots 31, 41, 51, and 61 show the stored output of transducer $T_R$ for such respective circumstances, and plots 32, 42, 52, and 62 show the corresponding Hilbert envelopes. It can be seen that hatched region 45, corresponding to the UBI-3 for a relatively porous bone, is much larger than hatched region 55, corresponding to the UBI-3 for a low-normal bone.

4. UBI-4

Figure 5A:
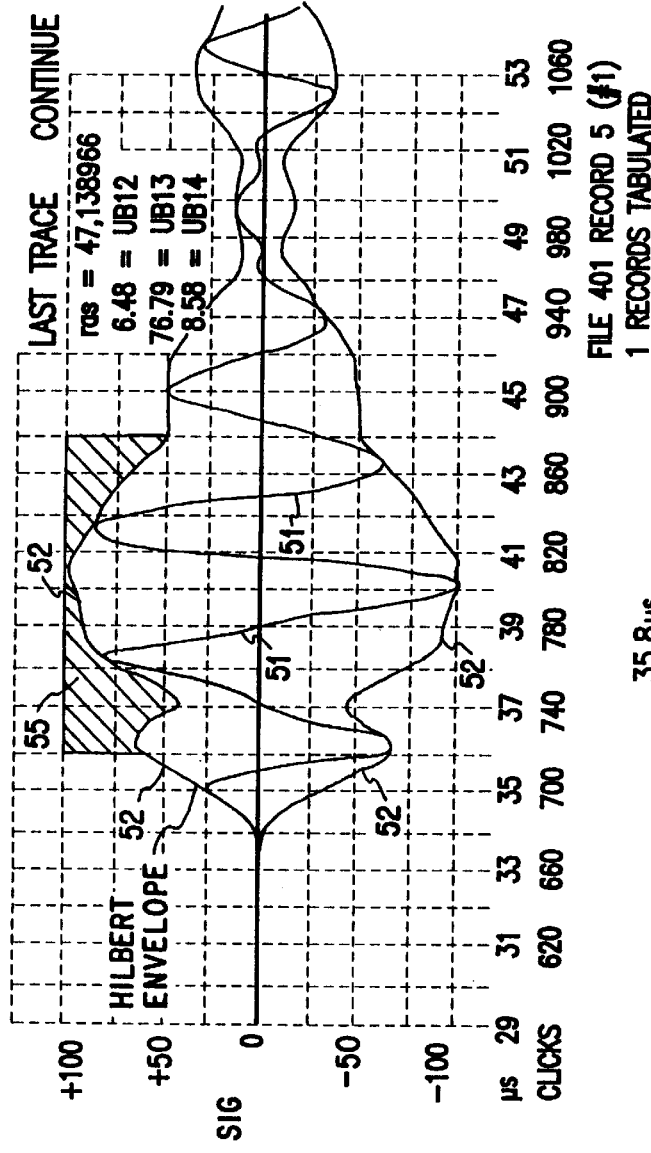
FIG. 5A provides a plot showing the stored output of transducer 13 of FIG. 1 in response to an excitation waveform, generated by the system of FIG. 1 and transmitted from transducer 12 through a bone of low-normal quality, as well as plots pertinent to calculation of UBIs in accordance with a preferred embodiment of the invention.
Figure 5B:
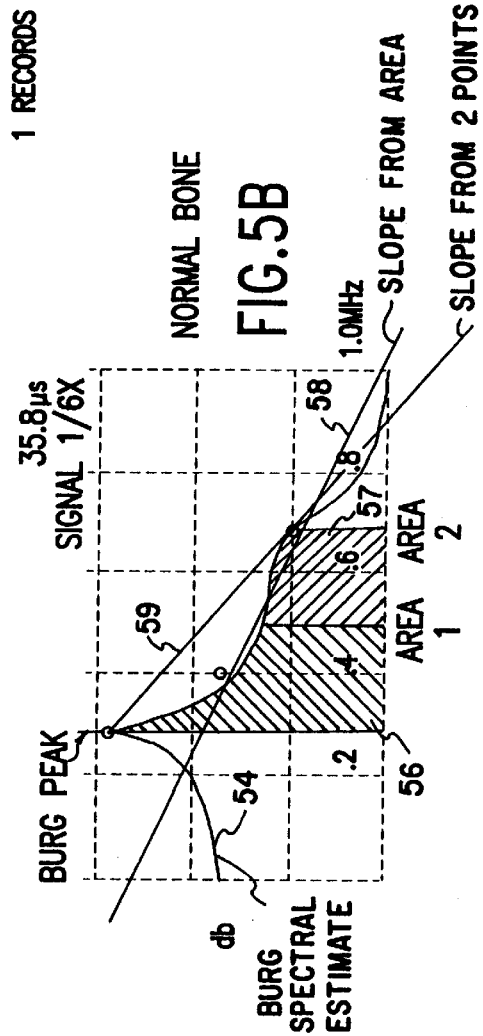
FIG. 5B provides a plot of the Burg spectral estimation function associated with the plots of FIG. 5A.
Figure 6A:
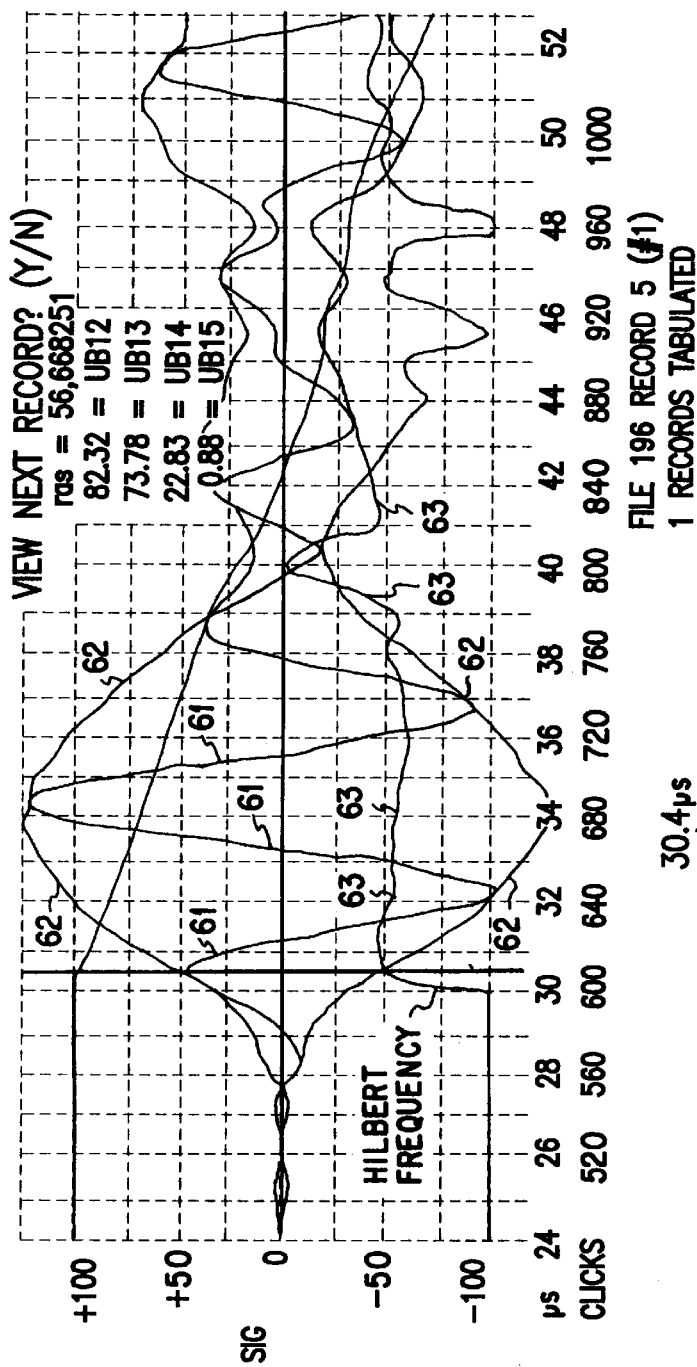
FIG. 6A provides a plot showing the stored output of transducer 13 FIG. 1 in response to an excitation waveform, generated by the system of FIG. 1 and transmitted from transducer 12 through an exceptionally healthy bone, as well as plots pertinent to calculation of UBIs in accordance with a preferred embodiment of the invention.
Figure 6B:
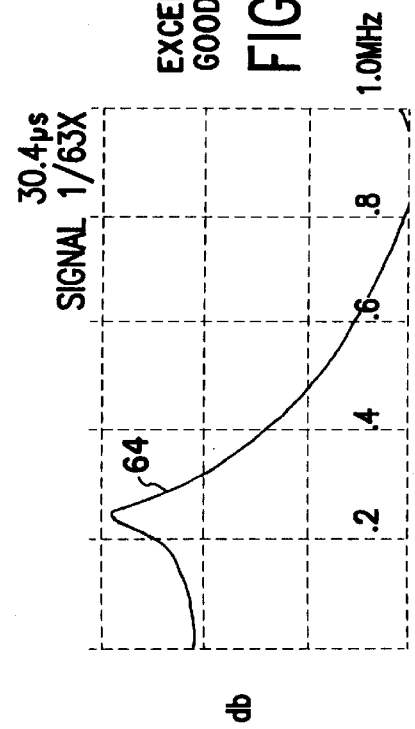
FIG. 6B provides a plot of the Burg spectral estimation function associated with the plots of FIG. 6A.

The UBI-4 procedure utilizes an autoregressive moving average (ARMA) spectral estimation function of the stored output of $T_R$. In one embodiment, UBI-4 uses the Burg spectral estimation function of the stored output of $T_R$; the Burg function provides a plot estimating power versus frequency of the received waveform. The shape of the plot is a discriminant between healthy and relatively porous bone. UBI-4 is an estimate of the slope; generally the more steeply negative the slope, the healthier the bone. In this connection, see plots 34, 44, 54, and 64 in FIGS. 3B, 4B, 5B, and 6B respectively for the case of transmission respectively through water, relatively porous bone, low-normal bone, and exceptionally healthy bone. In one embodiment, the UBI-4 slope of the plot is determined by best fit to the plot using mean square error. In another embodiment, the slope is determined in reference to the averages over two adjacent frequency regions, each of 200 kHz in width; the first frequency region starts at the first peak in the plot and the second frequency region starts 200 kHz higher. As an example, see areas 56 and 57 respectively in FIG. 5B, corresponding to the first and second regions. The proportional difference in these averages is indicative of the slope, which is shown as line 58 in FIG. 5B. In a further embodiment, the slope is determined by reference solely to two points on the plot, the first occurring at the first peak, and the second occurring 400 kHz higher in frequency. As an example, see line 59 in FIG. 5B.

5. UBI-5

The UBI-5 procedure estimates the instantaneous frequency during the early portion of the received waveform. One embodiment utilizes the Hilbert frequency function. This function is plotted as item 43 and 63 in FIGS. 4A and 6A respectively for relatively porous bone and exceptionally healthy bone respectively. It can be seen that for healthy bone, during the early portion (3 or 4 microseconds) of the received waveform, there is little variability, whereas for relatively porous bone, there is considerable variability including higher frequencies than for healthy bone. The variability can be quantified according to any of a variety of methods well-known in the art.

As an alternative, or in addition, to measuring the variability of the Hilbert frequency function with time, it is possible to determine the mean frequency of the first half-cycle of the received burst. (As is known in the art of signal processing, ordinary Fourier analysis cannot be used for, and is inapplicable to, such a short sample.) A comparison of the mean frequency indicated by curve 43 of FIG. 4A during the first half cycle of received signal and the mean frequency indicated by curve 63 of FIG. 6A during the first half cycle of received signal shows that the bad bone has a dramatically higher mean frequency during this half-cycle. One way of making this frequency determination is to labor through calculation of the Hilbert function over the course of this half-cycle and then determine its average over the interval.

Figure 20:
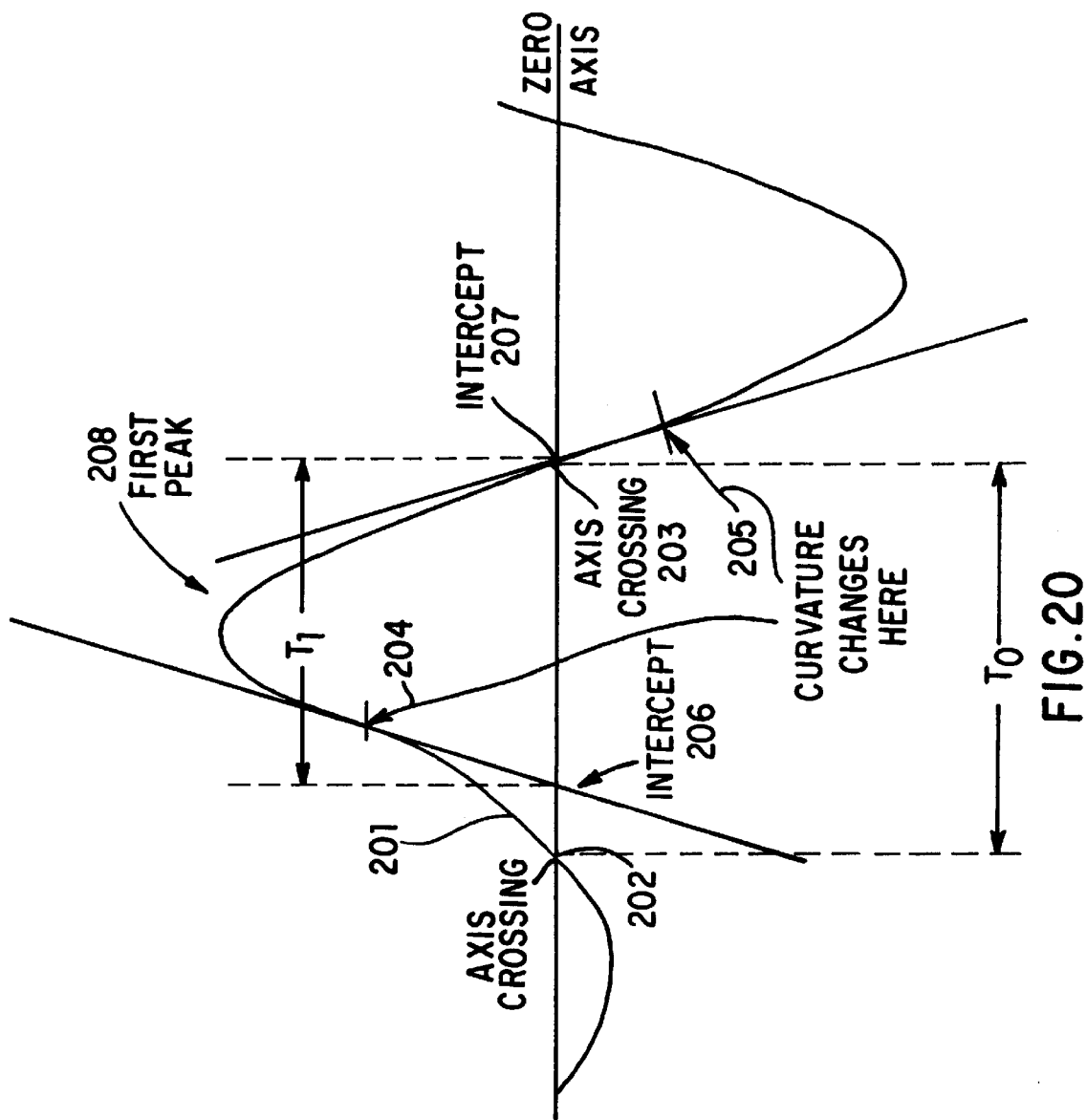
FIG. 20 illustrates a technique for estimating the instantaneous frequency of an early portion of the received signal in accordance with the procedure of UBI-5.

Alternatively, we have found that the average first half-cycle frequency can be estimated with good success. FIG. 20 illustrates a technique for estimating the instantaneous frequency of an early portion of the received signal in accordance with UBI-5. As shown in FIG. 20, merely using the zero crossings 202 and 203 of the received signal 201 produces a half-period $T_0$ that is too long (and a resulting frequency that is too low) to match the frequency most closely associated with the first half cycle. In other words, a sine wave having the half-period $T_0$ would be too broad to coincide with the first peak 208 of the received signal. We have found that a more accurate estimate of average frequency can be obtained by first identifying the points 204 and 205 on either side of the peak where the slope of the curve changes between increasing and decreasing (that is, where the second derivative with respect to time is zero). Next, the intercepts 206 and 207 of tangents to the signal curve at points 204 and 205 are determined. The duration between these intercepts 206 and 207 is the half-period $T_1$, which is used to determine the first half-cycle average frequency.

An alternative method of estimating the average first half-cycle frequency is to is to find the frequency that produces a least mean square error fit of a sine wave to a small zone surrounding an early peak 208.

6. UBI-6

The UBI-6 procedure utilizes the short-time Fourier transform of the stored output of $T_R$ to examine in more detail than with the Hilbert transform the varying spectral content of the received waveform over time. A frequency index may be computed in a fashion analogous UBI-2 or UBI-4. The temporal variation of this index may be used to compute a different index in a fashion analogous to UBI-5.

7. UBI-7

The UBI-7 procedure utilizes the Fourier transform of the stored output of $T_R$ to produce data permitting a plot of phase versus frequency; the slope of this plot is a measure of velocity (as a function of frequency). The variation of velocity with frequency (i.e., group delay) is dispersion, which can be quantified according to any of a variety of methods. In the relatively porous bone, there is relatively little dispersion; in relatively nonporous bone, there is relatively more dispersion.

8. UBI-8

The UBI-8 procedure is premised on the recognition that bad bone produces a broad band signature, whereas good bone tends to pass relatively low frequencies more selectively. Accordingly, UBI-8 involves the determination of (i) "narrow-band energy," which, for the purposes of this description and the following claims, is the energy associated with 100 khz of spectrum surrounding the low-frequency spectral peak, and (ii) "broad-band energy," which, for the purposes of this description and the following claims, is the energy associated with the full spectrum of 0–1000 kHz. UBI-8 is the normalized ratio of narrow-band energy to broad-band energy.

Figure 21:
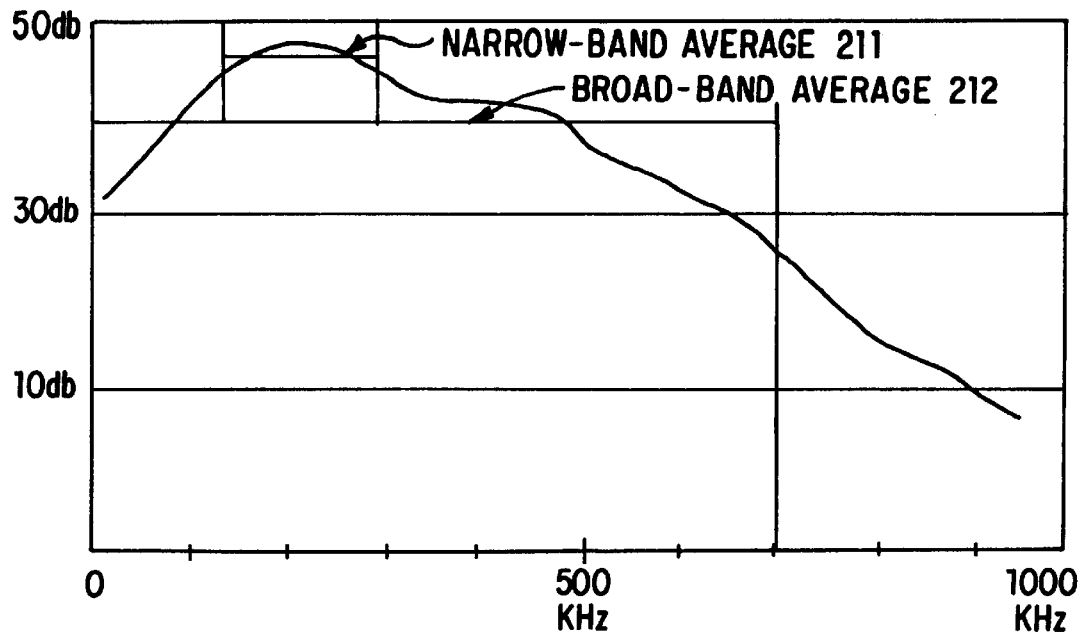
FIGS. 21 and 22 show the narrow-band energy and broad-band energy content of signals propagated through relatively porous and healthy bone respectively in connection with the procedure of UBI-8.
Figure 22:
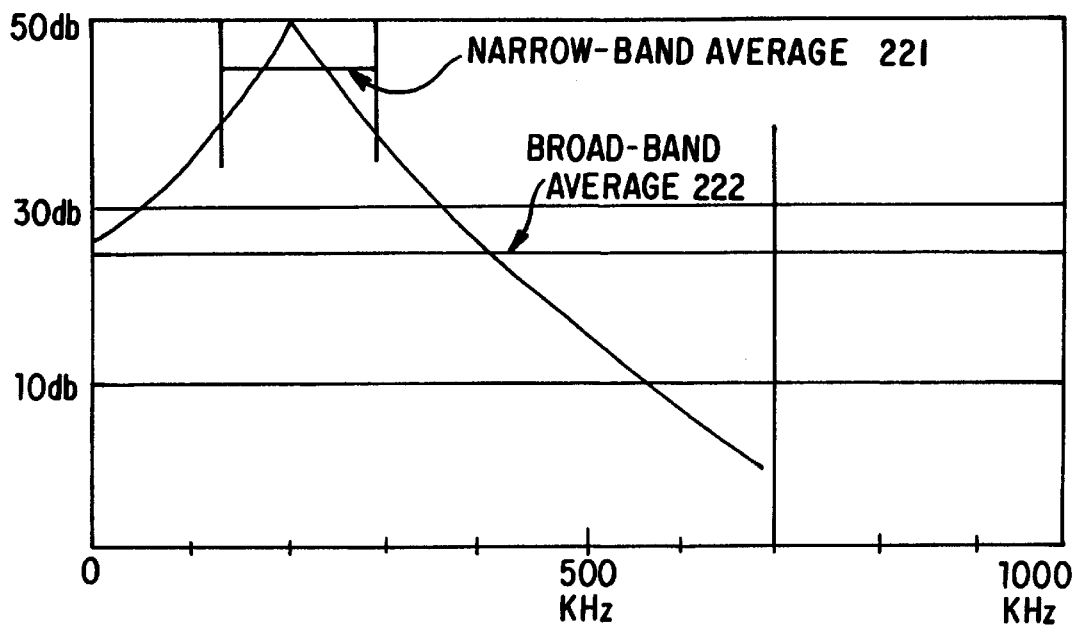

FIGS. 21 and 22 show the narrow-band energy and broad-band energy content of signals propagated through relatively porous and healthy bone respectively in connection with the UBI-8 procedure. The narrow-band averages for relatively porous and healthy bone are shown as line segments 211 and 221 respectively, and the associated narrow-band energy content in each case is the area under each of these segments. Similarly the wide-band averages for relatively porous and healthy bone are shown as line segments 212 and 222 respectively, and the associated wide-band energy content in each case is the area under each of these segments. Thus in the case of relatively porous bone in FIG. 21, the narrow-band energy content is about 10% of the wide-band energy content. In contrast, in the case of healthy bone in FIG. 22, the narrow-band energy content is much greater than 10% of the wide-band energy content.

9. Composite UBIs

Although any one of the UBIs discussed may be used alone, it is also possible to use combinations of any number of them to enhance sensitivity and specificity in identifying relatively porous bone. Indeed a single composite UBI may be derived as a function (which need not be linear) of the UBIs described above. The function may be the weighted sum, and the weights may be determined in the manner described above in connection with UBI-2: empirically, or using neural networks, or using the closed form analytical procedure described above.

In one embodiment, we have found it useful to take a UBI of the type described above and divide it by an estimate of heel width. The estimate can be derived from a determination of the delay between initiation of the burst in transducer $T_T$ and the arrival of the burst in the signal received by $T_R$. This quotient is therefore roughly normalized to take into account heel width.

10. Electronics

Figure 7:
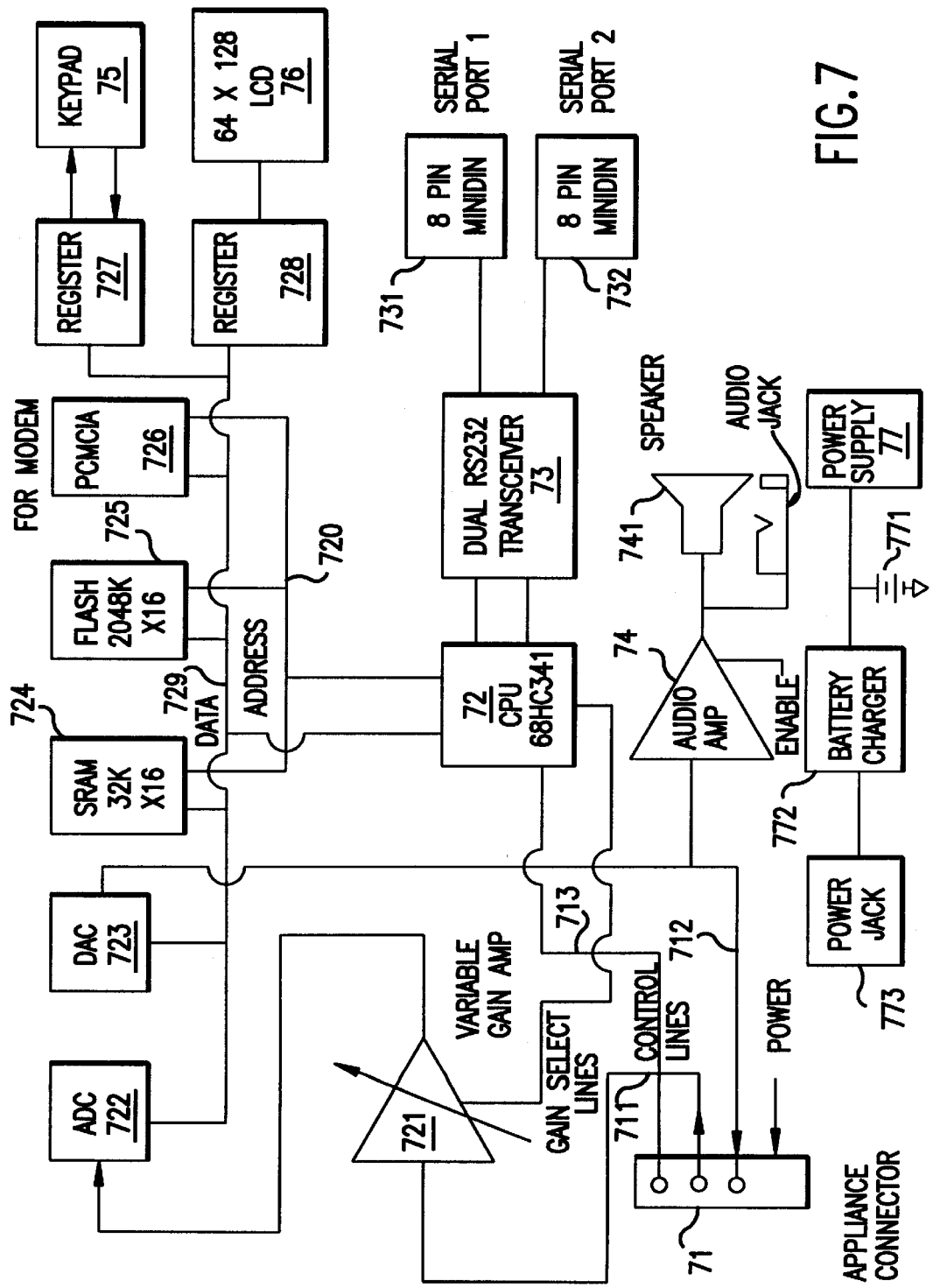
FIG. 7 is a diagram of a preferred embodiment of a hand-held implementation shown in FIG. 2.

The procedures described above may be employed in a device such as shown in FIG. 7, which is a diagram of a preferred embodiment of the implementation shown in FIG. 2. The device operates under the control of microprocessor 72, which is here implemented as a Motorola 68HC341. The microprocessor communicates with a data bus 729 and an address bus 720. In communication with these buses are static RAM 724 (here implemented as 32K times 16, to accommodate a 16-bit word), flash RAM 725 (here implemented as 2048K times 16), and PCMCIA slot 726 for communication via modem and potentially for other purposes. The device is also provided with first and second serial ports 731 and 732 respectively, coupled to the microprocessor 72 via dual RS232 transceiver 73, for data input and output, permitting attachment of an external modem and direct communication with a PC. User input to the device is achieved locally via keypad 75, coupled to register 727, which is on the data bus 729. The device has a video output on display 76, here an LCD bit-mapped display having a resolution of 64×128 pixels, that is in communication with register 728 and data bus 720. The excitation waveform to drive the transducer $T_T$ of FIG. 2 is stored in Flash RAM 725 and is loaded into static RAM 724 over data bus 729; the static RAM transfers the waveform by direct memory access (DMA) into digital-to-analog converter 723, which provides an output over line 912 to appliance connector 71 to drive the transducer $T_T$. The waveform output from transducer $T_R$ of FIG. 2 is communicated to line 711 of connector 71, and then through variable gain amplifier 721 to analog-to-digital converter 722. The gain of amplifier 721 is adjusted by the microprocessor 72 over gain select lines. The output of the converter 722 is communicated over data bus 729 to static RAM 724, where the received waveform data is captured. The data can then be processed by microprocessor 72 (according to the procedures described above), and UBI and other data can be presented to the user, both via the display 76 and over the ports 731, 732, and the PCMCIA slot 726. The transducers are here driven by a separate appliance module, described below in connection with FIGS. 8A and 8B, to which connection is made through appliance connector 71. The module is controlled by a dedicated microprocessor communication with which is over control line 713. Power is provided by power supply 77, which is coupled to battery 771 and battery charger 792, which in turn is connected to power jack 773.

In addition, we have found it valuable to provide a speaker 741 (audio jack 742 is also provided) coupled via audio amplifier 74 to digital-to-analog converter 723 to permit "listening" to the stored waveform received from transducer $T_R$. The listening is made possible by playing back the stored signal at 1/1000th of the original frequency and over an extended duration. The trained ear can distinguish many features of the waveform in this manner. The speaker can be used, moreover, similarly to listen to the waveform processed in other respects as well—processed, for example, in accordance with one or more of the UBI procedures described above. It can also be used to provide audible cues to the user, for example in positioning the appliance, so that a continuous analog signal indicative of position can guide the user, who will not then need to watch the display 76 while positioning the appliance.

Figure 8A:
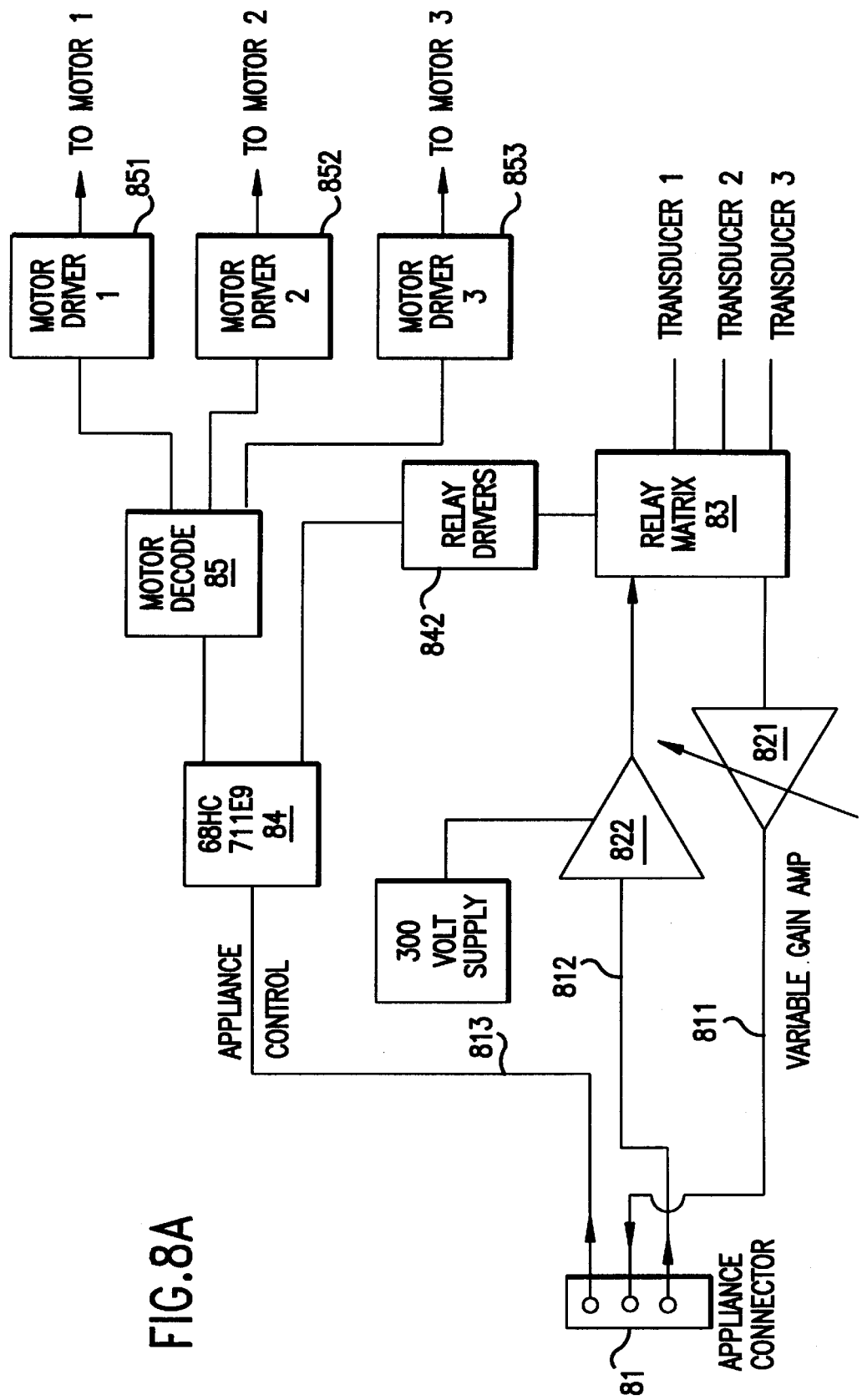
FIG. 8A is a diagram of a first embodiment of the appliance circuit module used in connection with the embodiment of FIG. 7.

FIG. 8A is a diagram of a first embodiment of the appliance circuit module used in connection with the embodiment of FIG. 7. The appliance connector 81 of FIG. 8 mates with connector 71 of FIG. 7. Control line 713 of FIG. 7 is connected through the connectors to control line 813 of FIG. 8, so that control signals run between slave microprocessor 84 (implemented here as Motorola 68HC711E9) and main microprocessor 72 of FIG. 7. The excitation line 712 of FIG. 7 is connected through the connectors to line 812 of FIG. 8 and driver amplifier 822, which is powered by a 300 volt supply. The received waveform line 711 of FIG. 7 is connected through the connectors to line 811 of FIG. 8A which receives an output from variable gain amplifier 821. The output of amplifier 822 and the input of amplifier 821 are connected to a relay matrix 83 that is driven by relay drivers 842 under control of microprocessor 84.

The relay matrix 83 permits the input of amplifier 821 to be connected to any of a series of, say, three transducers and the output of amplifier 822 to be connected to any other of the series of transducers. This arrangement has the advantage that the specific transducers used for transducers $T_T$ and $T_R$ may be switched, as desired, to assure symmetry of the system in either configuration and/or to compensate for the lack of symmetry. It also permits the use of a third transducer for a variety of purposes, including those described in U.S. Pat. 5,396,891, wherein three transducers are used in velocity measurements.

We have also found that when two transducers (producing preferably in this case a columnated beam) are used for ultrasound signal transmission, a substantial portion of the waveform energy not transmitted directly through the calcaneus can be detected by positioning a third transducer in a position distinct from the second transducer around the periphery of the heel to receive scattered or backscattered acoustic radiation. The signal from this third transducer can provide information complementary to, or overlapping, that obtained with the initial two transducers associated with direct transmission.

The microprocessor 84 also communicates optionally with motor decoder 85, which is coupled to drivers 851, 852, and 853 for motors 1, 2, and 3 respectively. These motors control the position of the transducers relative to the body part including the bone under measurement. The motors may be usefully used to assure correct positioning of the transducers for the measurements being made. Indeed, it appears that relative porosity may appear preferentially not only in certain bones of a subject but also in one or more regions of such certain bone, such as the calcaneus. In accordance with an embodiment of the present invention, one or more of the transducers $T_T$ and $T_R$—and (in a further embodiment) both such transducers—are moved, over a pertinent region of the bone, either by the user or under microprocessor control, until an optimized reading (determined by one or more of the above procedures or otherwise) has been obtained, and then the measurements in the position associated with this optimized reading in accordance with the above procedures are completed and stored.

Figure 8B:
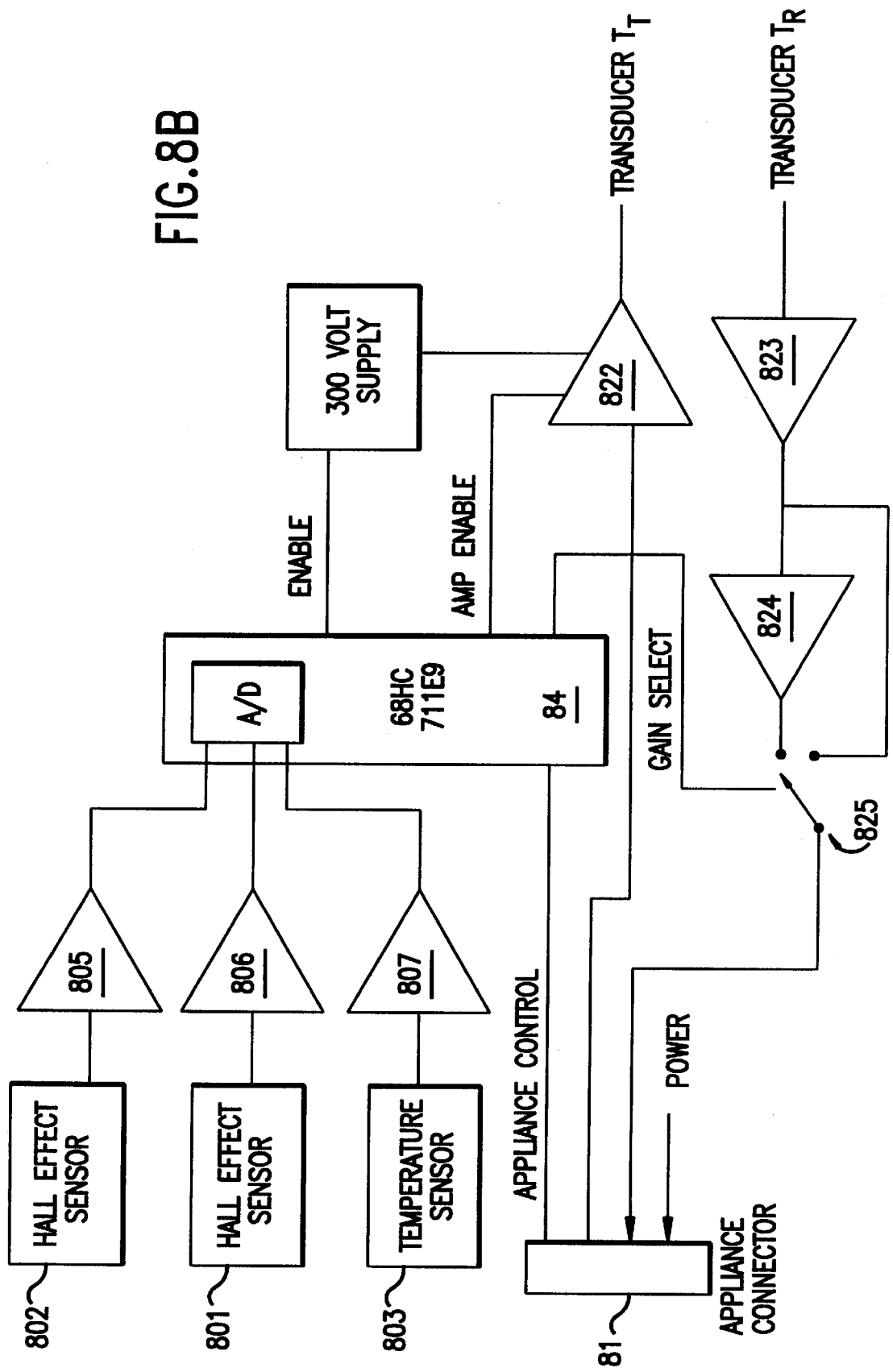
FIG. 8B is a diagram of a second embodiment of the appliance circuit module used in connection with the embodiment of FIG. 7.

FIG. 8B is a diagram of a second embodiment of the appliance circuit module used in connection with the embodiment of FIG. 7. In this embodiment, the motor drive circuits have been eliminated, only two transducers are employed, and these transducers, $T_T$ and $T_R$, are moved manually utilizing the appliance described below in connection with (for example) FIG. 10. Additionally, there are provided a pair of Hall effect sensors 801 and 802 to sense position (as described in connection with FIG. 11) of the transducers and a temperature sensor 803 to enable temperature compensation; the outputs of these transducers are amplified by amplifiers 806, 805, and 807 respectively, converted to digital format by an A-to-D converter associated with microprocessor 84, and then used as processing inputs. Gain for amplification of the signal received by transducer $T_R$ is adjusted by the microprocessor-controlled switch 825, which in a first position is connected to the output of first amplifier 823, and in a second position is connected to the output of second amplifier 824, which as its input the output of amplifier 823.

Figure 9:
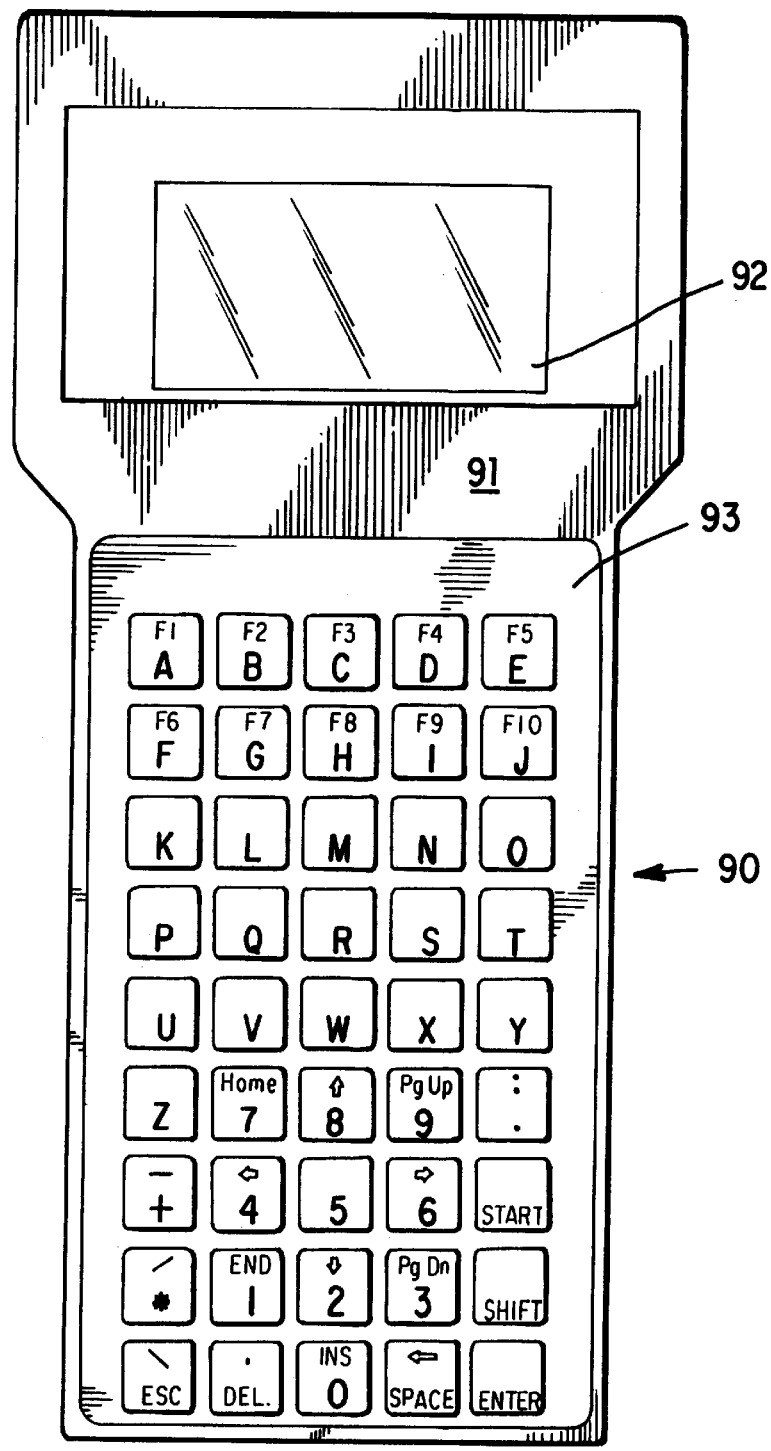
FIG. 9 is a front view of a hand-held device according to the embodiment of FIG. 7.

FIG. 9 is a front-view of a hand-held device 90 according to the embodiment of FIG. 7. All of the circuitry of the device of FIG. 7 is contained in a single unit, permitting excitation of the appliance transmitting transducer and processing of waveform data from the appliance receiving transducer(s) and storage and display of the results. The device has a housing 91, in which is provided the display 92 (item 76 of FIG. 7) and keypad 93 (item 75 of FIG. 7). The device also has the ports and other features described above in connection with FIG. 7.

11. Appliance

Figure 10:
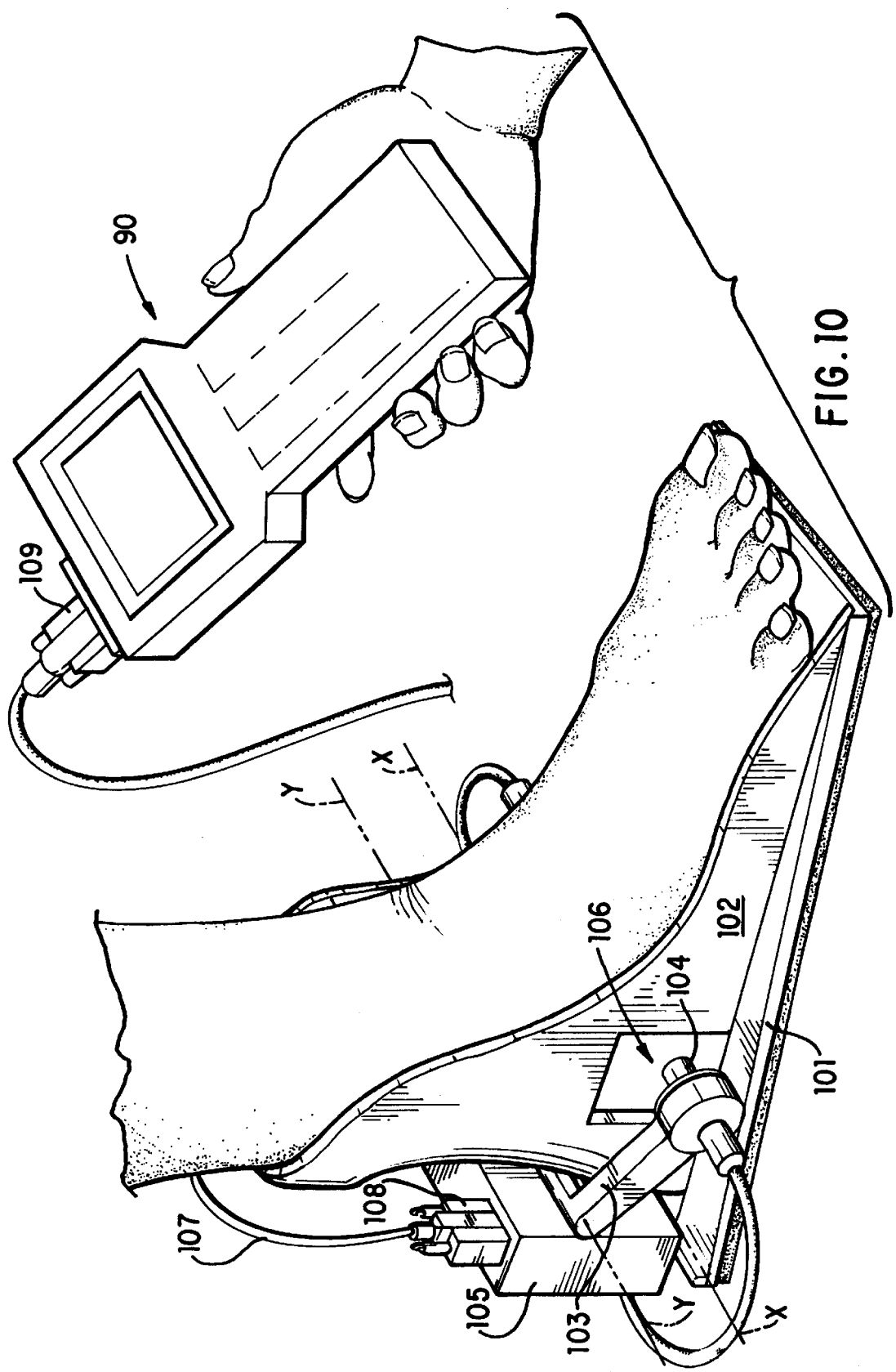
FIG. 10 is a side perspective view of an appliance in accordance with an embodiment of the invention.

FIG. 10 is a side perspective view of an appliance in accordance with an embodiment of the invention. The appliance includes a base 101 to which is attached rigidly a cradle 102 for the subject's foot and ankle. The subject's heel (and, if desired, neighboring regions) may be bare, or it may be placed, for purposes of hygiene, in a glove-like covering. To assure good ultrasound conduction, the covering is preferably thin, tight-fitting, and elastic. Alternatively, or in addition, the covering may be coated on the inside with a suitable material, such as a water-based gel, to assist in ultrasound conduction. (The effects of these materials may be compensated in signal processing of the received waveform.) The region of the cradle 102 corresponding to the calcaneus includes a cutout 106 on each side to accommodate a receiving transducer on one side and a transmitting transducer on the other side. The transducers are mounted in generally opposed relation to one another (in location 104 for the lateral transducer) in a yoke 103 that is movably mounted relative to the base 101 and cradle 102. In this embodiment the yoke 103 has two degrees of freedom, achieved by mounting the yoke 103 via a hinge at axis Y—Y to backplate 105, and mounting the backplate 105 via a hinge at axis X—X to the base 101. The appliance module of FIG. 8B is here physically mounted inside the backplate 105. Cable 107 with connectors 108 and 109 permits communication respectively between the appliance module and the hand held device 90 described in connection with FIG. 9 and provides power to the appliance module from the device 90.

The position of the transducers may be monitored by using potentiometers, shaft encoders, or other suitable sensors disposed in relation to the axes X—X and Y—Y. In addition, the sensors are preferably biased inwardly toward each other (by one or more springs or other means) to assure good contact with the heel area of the subject for ultrasound transmission. If desired, the distance between the transducers can be determined indirectly, by mounting each transducer on a separate arm that is pivotally mounted at one end to the yoke, and the angle that the arm makes at the pivot can be monitored by suitable sensors; the arm angles, in combination with a knowledge of the geometry of the yoke assembly, can be used to calculated the distance between the transducers. Such distance information is useful for ultrasound velocity determinations and for normalization of UBI values.

Positioning of the transducers in relation to the axes X—X and Y—Y is important to assure that the transducers are located away from edges of the calcaneus. We have found that positioning the transducers near an edge of the calcaneus has a profound effect on the received waveform. Furthermore, we have found that appropriate signal processing of the received waveform permits one to detect proximity to an edge of the calcaneus, so that the transducers may be located in a position, away from the edge, that results in signal transmission and reception through a central region of the calcaneus.

Figure 23:
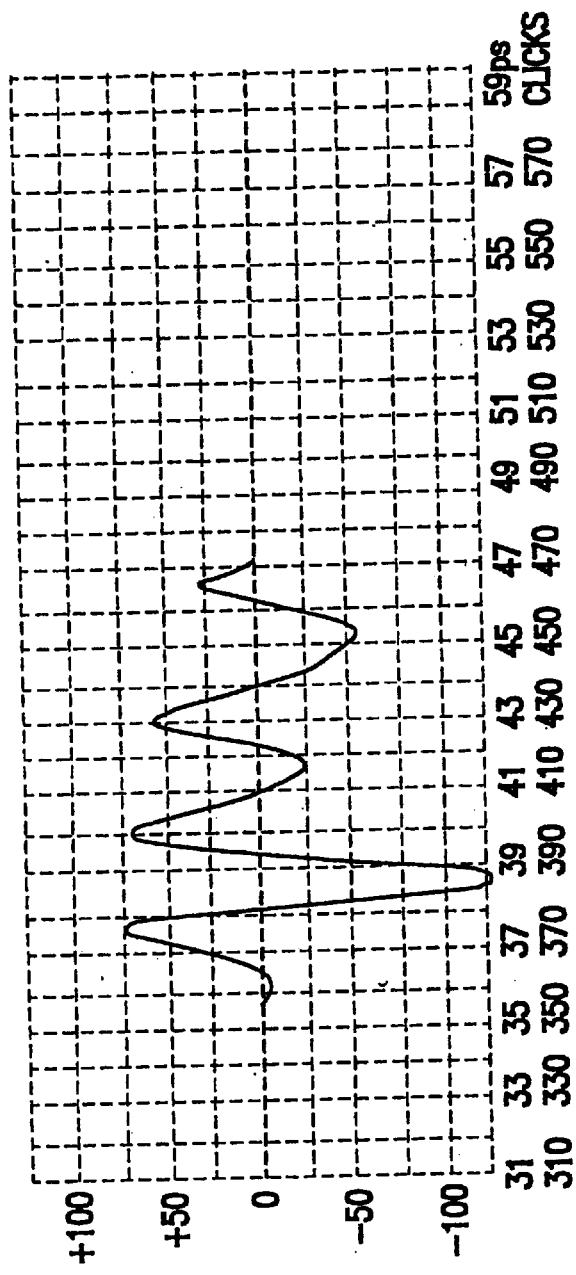
FIGS. 23 and 24 show the time and frequency domain content of a typical waveform received on a path respectively through a central region (shown in FIG. 23) and near the edge (shown in FIG. 24) of healthy calcaneus bone.
Figure 23:
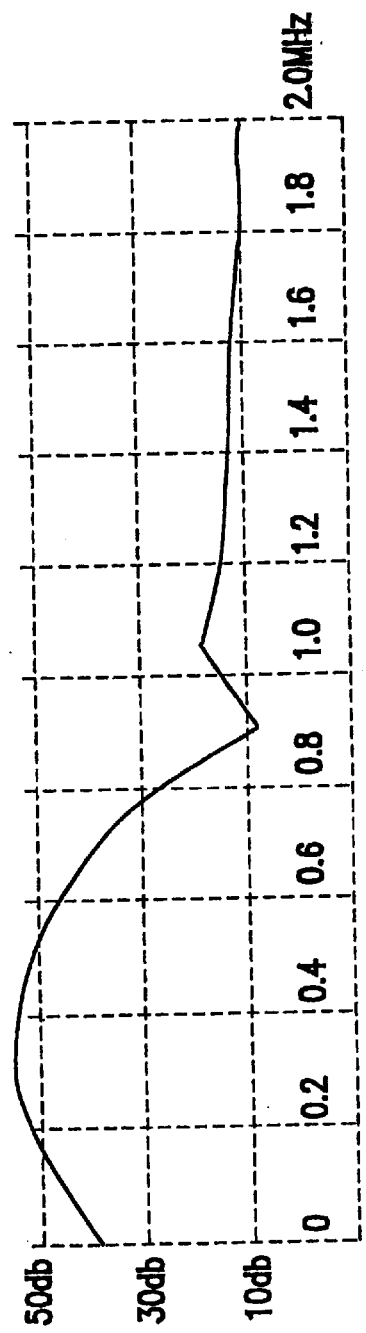
Figure 24:
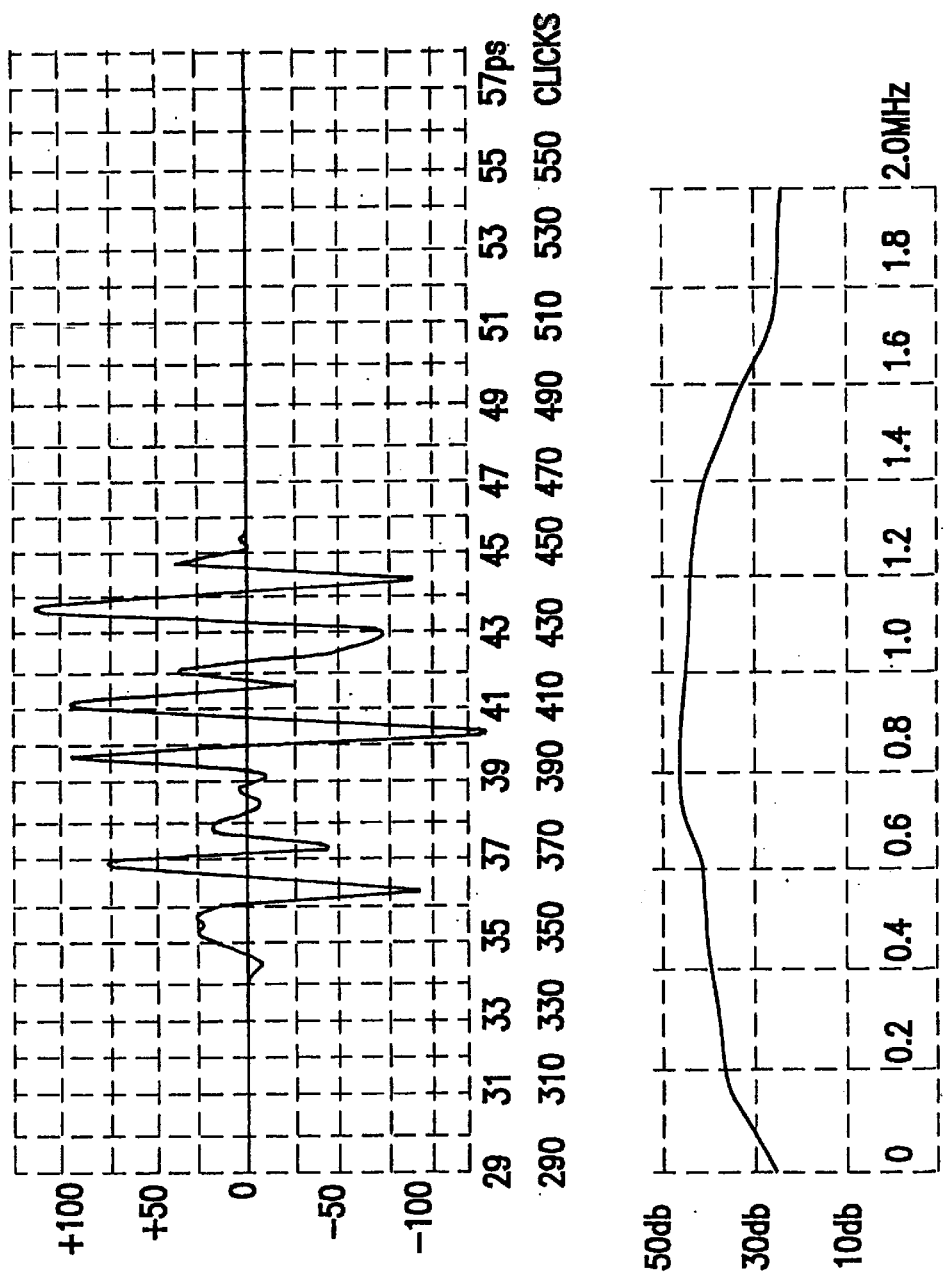

For detection of an edge of the calcaneus it is possible to utilize one or more UBI values determined in the manner described above. For example, when the ultrasound path is near the edge of a bone or predominantly in soft tissue, the various UBI values will result in an index identifying relatively porous and non-connective bone. Alternatively, we have found that quantifying the relative amount of energy in the received waveform at high frequencies in relation to that at low frequencies produces a test that is particularly sensitive to bone edges. This phenomenon is illustrated in FIGS. 23 and 24. In FIGS. 23 and 24 are shown the time and frequency domain content of a typical waveform (as discussed in connection with the embodiments above) received on a path respectively through a central region (shown in FIG. 23) and near the edge (shown in FIG. 24) of healthy calcaneus bone. It can be seen in FIG. 23 that the energy in the received waveform on a central path is concentrated below about 800 KHz, whereas the energy in the received waveform on the edge path (in FIG. 24) is rich in high frequencies. The relative absence of high frequencies associated with positioning of the signal path away from the edge can be quantified in various ways. One usable test is to compute the fraction of high frequency energy (defined here and in the claims as energy at frequencies between approximately 900 KHz and approximately 1.2 MHz) in relation to the low frequency energy (defined here and in the claims as energy at frequencies between approximately 300 and approximately 600 KHz) in the received signal. In the case of FIG. 23, the fraction is less than 1%, whereas in FIG. 24 the fraction is over 100%. This test can be used to determine appropriate positioning of the signal path (by motion of the yoke 103 of FIG. 10). The test may be conducted in real time to determine appropriate positioning, or alternatively, since the received signal can be sampled and stored, one may record the waveforms for a variety of transducer positions, and thereafter select the recorded waveform or waveforms that indicate appropriate positioning; the selected waveform or waveforms can then furnish the basis for the UBI determination as described above.

Figure 11:
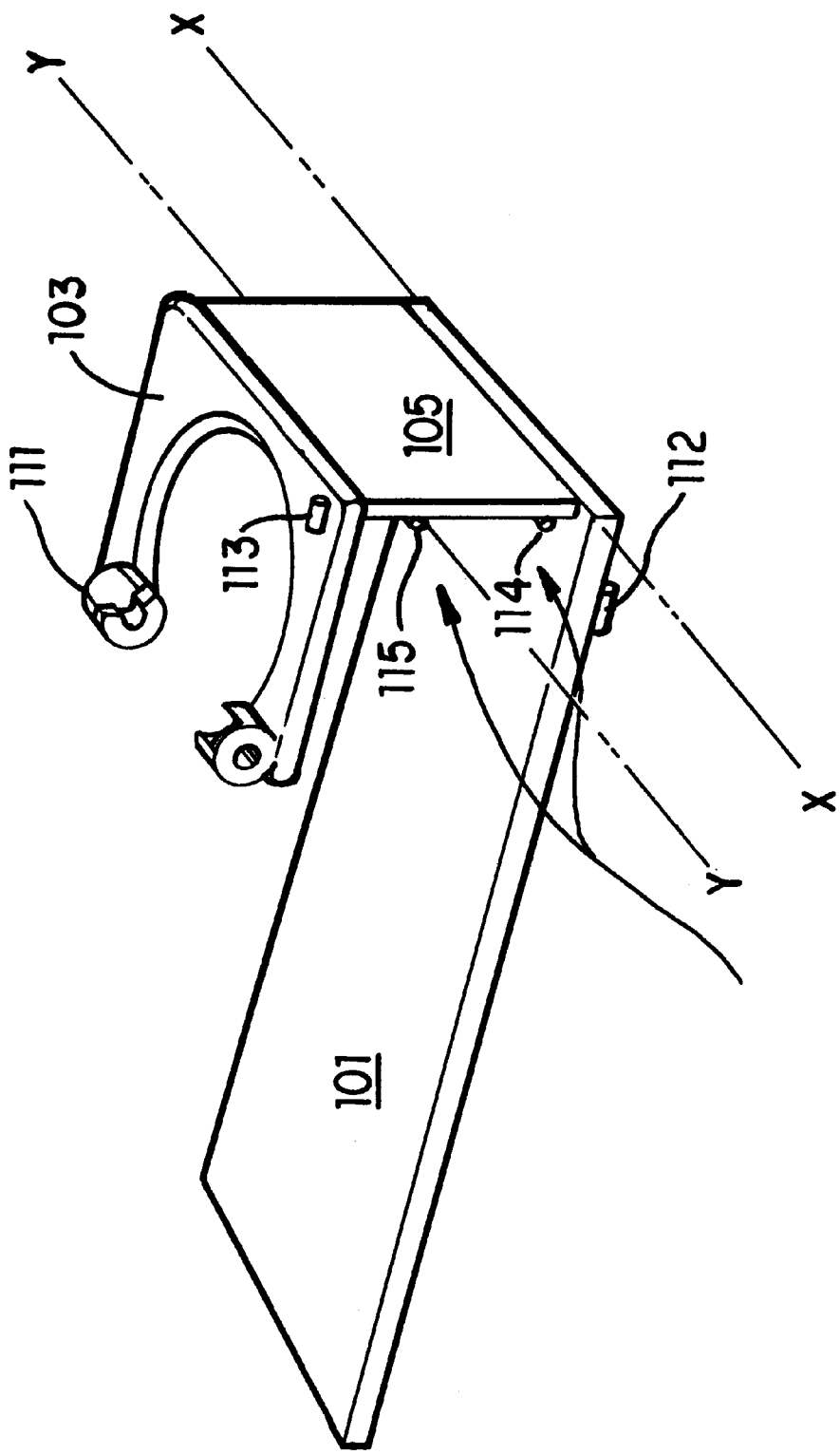
FIG. 11 shows an embodiment of the appliance of FIG. 10, equipped with magnets and hall effect devices to monitor the location of the transducers.

FIG. 11 shows an embodiment of the appliance of FIG. 10, equipped with magnets and Hall effect devices to monitor the location of the transducers, mounted in the yoke 103, in holders 111. In this embodiment a first ceramic magnet 112 is mounted on the base 101 and a second ceramic magnet 113 is mounted on the yoke 103. Hall effect magnetic sensors 114 and 115 are mounted on stalks on backplate 105 in to detect the magnetic fields of magnets 112 and 113 respectively. The signal strengths of the outputs from Hall effect sensors 114 and 115 are therefore indicative of the degree of rotation respectively of backplate 105 about axis X—X and of yoke 103 about axis Y—Y. These outputs are linearized with angle by geometrically aligning each magnet and sensor pair so as to combine the 1/r effect (at these distances) of magnet-sensor distance and the sine θ effect of sensor angle in the magnetic field. Accordingly, the outputs of Hall effect sensors can be mapped, under microprocessor control, into suitable rectangular coordinates to identify the location of the transducers in relation to the subject's heel.

As discussed above in connection with FIGS. 8A and 8B, the yoke may be moved manually or it may be moved under motor control by suitably mounted motors associated with each degree of freedom.

FIGS. 12, 13, and 14 provide top, rear, and side views respectively of the foot of a subject in relation to a transducer pair $T_T$ and $T_R$ to illustrate orientation of the transducers in connection with a preferred embodiment of the present invention. Here the separate transducers $T_T$ and $T_R$ are here generically identified as $T_a$ regardless of function. Because the transducers act approximately as point sources and point receivers—unlike transducers used in prior art devices—they need not be placed in coaxial alignment. Indeed, it is desirable that they be oriented so as to be approximately normal to the surface of the heel at the point of contact with the heel. The effect of placement in this orientation is that the axes of the transducers are not coaxial; the axes are skewed with respect to one another in two distinct planes, the horizontal and the vertical. In FIG. 12 the line through the two points of contact of the transducers with the heel is shown as A—A. The central longitudinal axis of each transducer is shown as P. It can be seen that each transducer axis P is oriented in a rearward direction with respect to the points of contact axis A—A by an angle θ, which in practice is about 20 degrees. Similarly, shown in FIG. 13 is a rear view of the foot of a subject including the medial malleolus 131 and lateral malleolus 132. In this view it can be seen that each transducer axis P is oriented in an upward direction with respect to the points of contact axis A—A by an angle Φ, which in practice is about 10 degrees. As shown in connection with the side view in FIG. 14, the effect of this orientation is each transducer points both down and forward in order to be approximately normal to the heel at the point of contact. This orientation can be achieved by appropriate configuration of the yoke 103 and related components in FIGS. 10 and 11.

Figure 15:
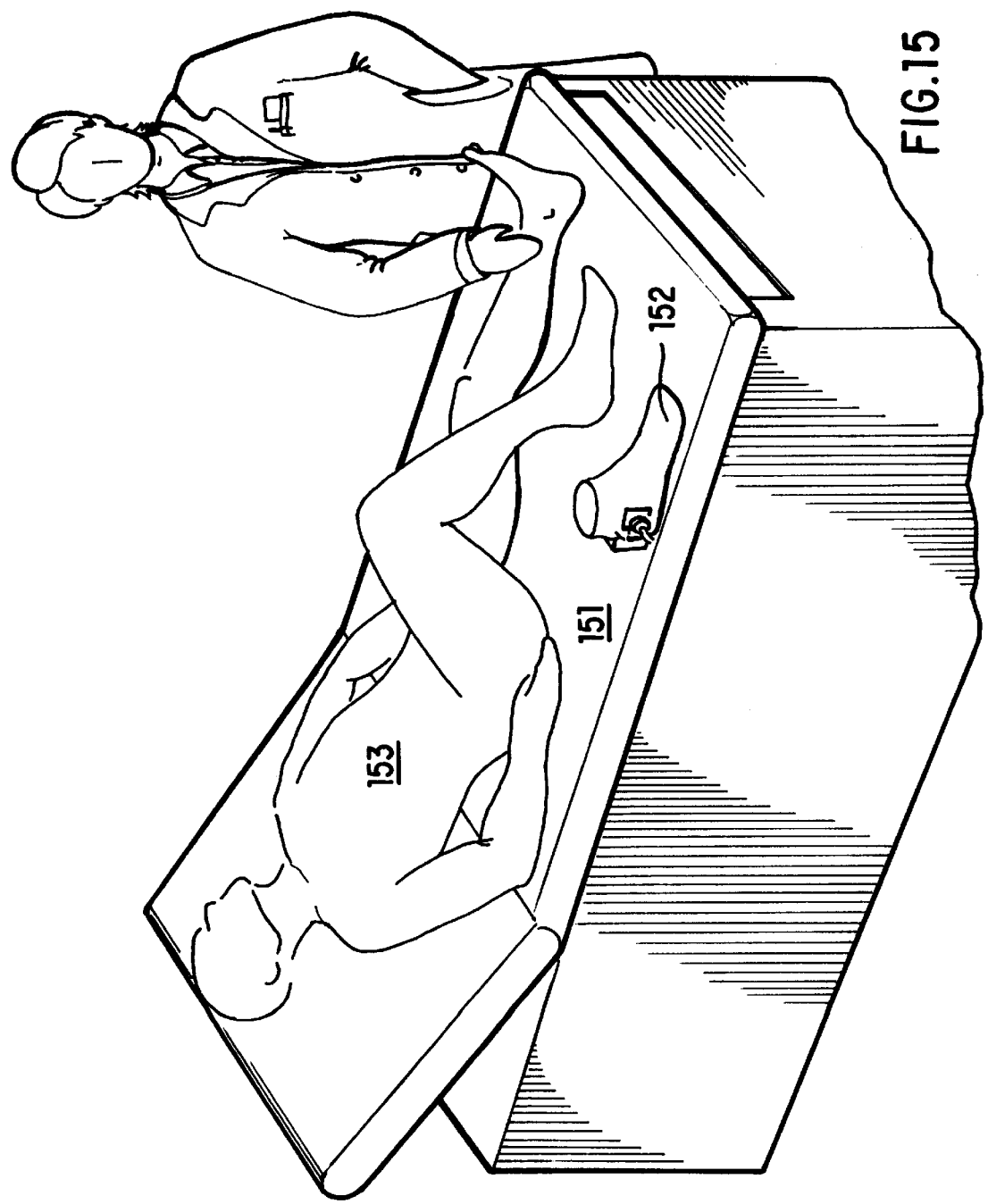
FIG. 15 shows a further embodiment of the invention wherein the subject 153 to be tested may occupy a generally horizontal position.

While an advantage of the appliance illustrated in FIGS. 10 and 11 is that the subject may be tested when the subject is either standing or seated with feet on the floor, there is an attendant disadvantage in that the subject's foot is difficult to immobilize in the appliance when the subject is in such a position. In a further embodiment of the invention, shown in FIG. 15, the subject 153 to be tested may occupy a generally horizontal position on a conventional physician's examination table 151 or other horizontal surface. The appliance 152 may thus be fitted onto the subject 153 when the subject is lying on the back. When the subject's foot is extended after the appliance 152 is fitted onto the subject, the foot is supported both by the appliance 152 and by the examination table 151 and is less prone to movement within the appliance 152.

Figure 16:
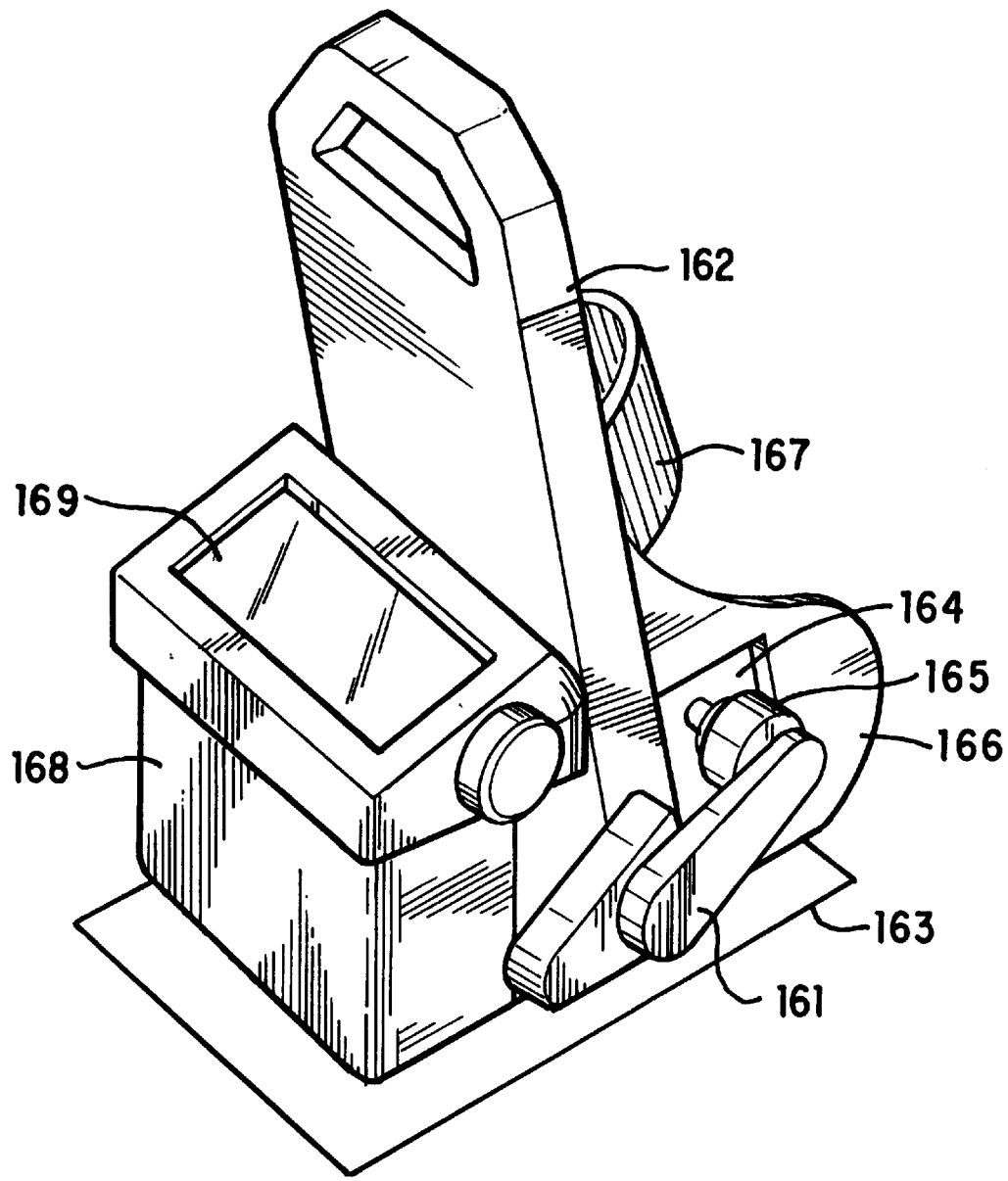
FIG. 16 illustrates in perspective, from a bottom view, an appliance suitable for use in testing a prone subject.

In FIG. 16 is illustrated in perspective, from a bottom view, an appliance suitable for use in testing a prone subject. The appliance is configured and used in the general manner of the appliance of FIGS. 10 and 11. The appliance here has a base 162 to which is rigidly attached a cradle 166 for the subject's foot and ankle. In this embodiment, however, the base 162 is itself rigidly mounted to horizontal support 163, which typically rests on the examination table 151 of FIG. 15. Strap 167 may be used to removably secure the subject's foot in the cradle 166. The cradle 166 includes a cutout on each side in the region corresponding to the calcaneus to accommodate the transducers $T_T$ and $T_R$, which are mounted to yoke 161 on opposite sides of the calcaneus; the yoke 161 is movably mounted with respect to base 162 and support 163. As in the case of the appliance FIGS. 10 and 11, the transducers may be moved manually or by motors under control of a microprocessor. Case 168 may be used to hold the appliance module of FIG. 8A or 8B. Alternatively, case 168 may house the equivalent of both the appliance module and the device of FIG. 7. In the latter case, the case 168 may be fitted with display 169, a keyboard, etc. It is also within the scope of the present invention to have the appliance operate in wireless communication (using rf or infra red) with a base unit that may but need not be hand held or hand-holdable, and in such an instance, the display 169 can be used to indicate the presence of satisfactory orientation of the appliance and the transducers or to provide other pertinent information to the operator.

Figure 17:
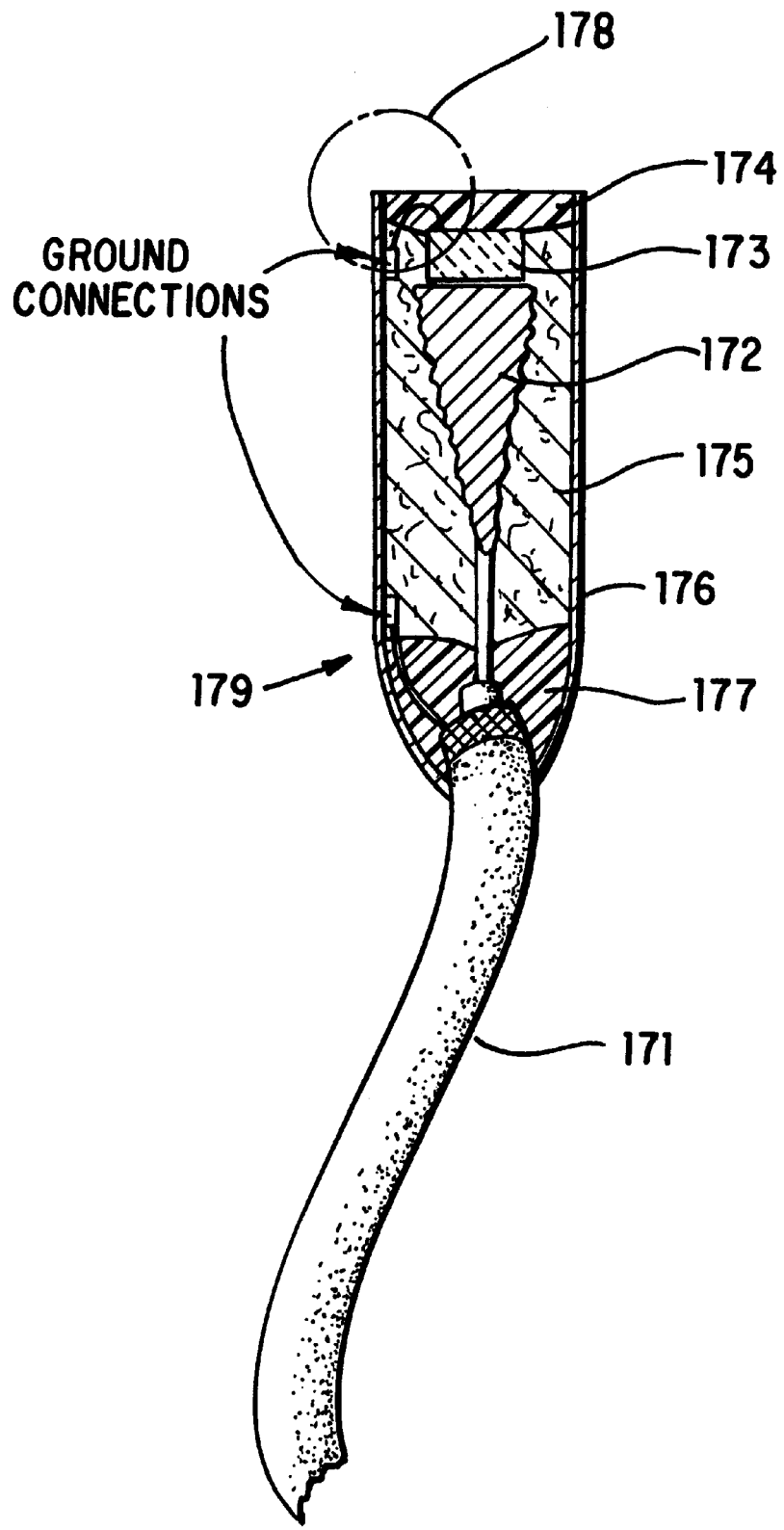
FIG. 17 is a cross-section of a transducer suitable for use in the appliance of FIGS. 10 and 11.

FIG. 17 is a cross-section of a transducer suitable for use in the appliance of FIG. 10. The transducer utilizes a piezoelectric crystal element 173, which is unusual in that its aspect ratio is of the order 1.5:1. (As used in this description and the following claims, "aspect ratio" is the ratio of diameter to thickness.) Such a ratio is usually viewed as undesirable, and more typical aspect ratios are at least 5 or 10:1, so as to avoid undesirable resonances in directions other than the transverse plane from which the ultrasound is to be propagated. In the present case, however, we have found that our design adequately controls multiple resonances and yields desirable near point-source behavior and wide bandwidth. Typical dimensions for a piezoelectric element of our design are a diameter of 0.125 inches (0.32 cm) and a thickness of 0.080 inches (0.20 cm). The element rests between metal base 172 and front face element 174, which are connected to the center and outside conductors respectively of a suitable coaxial cable 171. The front face 174 plays a role in the frequency response of the transducer, and its thickness is chosen empirically to optimize the frequency response. In practice, it has been found desirable to construct the front face 174 of epoxy with a thickness of 0.025 inches (0.6 mm). The transducer is disposed in a housing 176; the housing serves as both a mechanical anchor for the transducer and as an electrical shield, and is preferably of a metal, such as, for example, brass. The base 172 is placed within acoustically absorbent backing 175 to damp ringing, and the back end of the assembly is held in place with epoxy 177.

Figures 18, 19:
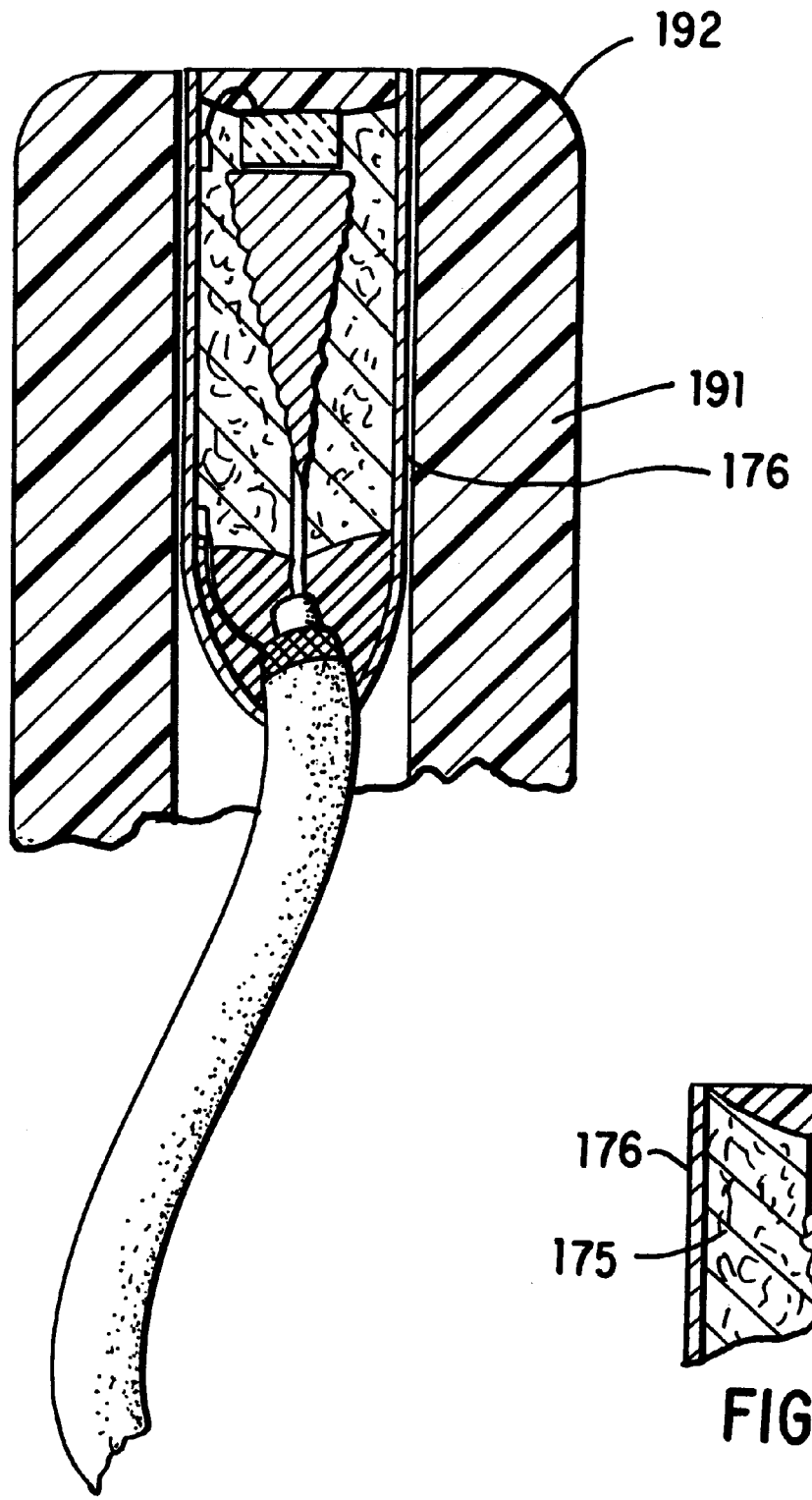
FIG. 18 shows detail of the region 178 in an alternative embodiment of the transducer of FIG. 17.
FIG. 19 shows the transducer of FIG. 17 surrounded by a sleeve 191.

FIG. 19 shows the transducer of FIG. 17 surrounded by a sleeve 191. In mounting the transducer 17 of FIG. 17 in the yoke 103 of FIG. 10, we have found it beneficial to surround the case 176 with a sleeve 191 of a suitable material such as Delrin plastic. The collar serves not only to receive spring pressure for spring-loading against the body but also to deflect ultrasound in a desired direction. The sleeve 191 may be sealed against the case of the transducer with a material such as silicon rubber. Alternatively, the sleeve may be made of metal and integrally formed with the case 176. A typical thickness of the sleeve wall is approximately ¼ inch (6 mm). As shown in FIG. 19, the end of the sleeve providing an opening to the transducer has an outside perimeter 192 that is preferably rounded.

FIG. 18 shows detail of the region 178 in an alternative embodiment of the transducer of FIG. 17. In FIG. 18, the absorbent backing 175 is extended into the area around the perimeter of the piezoelectric element 173 that is adjacent to and in front of it. The effect of this additional backing material is reduce the extent of epoxy around the perimeter of the face to better direct ultrasound energy toward the subject.

The transducer of FIG. 17 produces an excitation area that is about an order of magnitude smaller than the 3 cm beam produced by typical transducers used in prior art devices for measuring bone soundness. Moreover, in the preferred embodiments of the present invention, the transducer is engaged proximately to the calcaneus, whereas in many prior art devices, the transducer is spaced in the vicinity of 5 cm or more from the surface of the heel. Given the relatively small area—about 5 cm in diameter—of the target calcaneus bone, the large beam signature of the prior art transducers is subject to greater contamination by the effects of the bone boundary. Use of the transducer of FIG. 17 as the transmitter approximates the behavior of a point source, and use of a similar transducer as the receiver approximates the behavior of a point receiver, so that effects of the bone boundary may be minimized. Furthermore, the transducer of this design radiates and receives effectively over a wide angular range, permitting optimization of direct coupling to the body part based on anatomical features rather than on the need to maintain coaxial orientation as in the case of prior art transducers.

What is claimed is:

1. A system for externally providing a measurement in a vertebrate subject of the characteristic behavior of an acoustic wave in a bone disposed within a foot having a longitudinal axis, the system comprising:
   a. a base having a surface for receiving the sole of the foot;
   b. first and second transducers mountable in spaced relationship with respect to the bone;
   c. signal excitation means for causing the first transducer to produce an acoustic waveform that is propagated into the subject and received by the second transducer along a path that includes the bone;
   d. characteristic determination means for determining a characteristic of the behavior of the waveform along the path;
   e. a display for displaying outputs of the characteristic determination means;
   f. a first assembly containing the base and the transducers; and
   g. a second assembly, containing the display, that is hand-holdable and permits the measurement to be taken while holding the second assembly in one hand of the user, wherein the signal excitation means and the characteristic determination means are collectively contained within the first and second assemblies.

2. A system according to claim 1, wherein the characteristic determination means includes a signal processor for providing a single measurement that is a function of at least one of spectral or temporal components of a portion, up to the whole amount thereof, of the signal received by the second transducer.

3. A system according to claim 1, wherein the first assembly further includes:
   a. a cradle rigidly attached to the base, for receiving the subject's foot and ankle, and disposed in a direction transverse to the base;
   b. a yoke for supporting the transducers in spaced relationship with respect to the bone; and
   c. a member for mounting the yoke in moveable relationship to the base so as to permit joint two-dimensional motion of the transducers over regions of the heel including the calcaneous.

4. A system according to claim 3, wherein:
   the member is a backplate hingedly attached at one end to the base along a first hinge axis generally transverse to the longitudinal axis; and
   the other end of the backplate is hingedly attached, along a second hinge axis generally parallel to the first hinge axis, to the yoke.

5. An appliance for removable engagement with the foot of a subject, the appliance having:
   (a) a base having a surface for receiving the sole of a foot having a longitudinal axis;
   (b) a cradle rigidly attached to the base, for receiving the subject's foot and ankle, and disposed in a direction transverse to the base;
   (c) a yoke for supporting a pair of transducers in spaced relationship with respect to the heel of the foot;
   (d) a member for mounting the yoke in moveable relationship to the base so as to permit joint two-dimensional motion of the transducers over regions of the heel including the calcaneus.

6. An appliance according to claim 5, wherein:
   the member is a backplate hingedly attached at one end to the base along a first hinge axis generally transverse to the longitudinal axis; and
   the other end of the backplate is hingedly attached, along a second hinge axis generally parallel to the first hinge axis, to the yoke.

7. An appliance according to claim 5, further comprising:
   a control module, physically mounted to at least one of the base, cradle, yoke or member, the module having a first set of data ports coupled to the transducers, a second set of data ports for coupling to (i) a signal excitation means for causing a first one of the transducers to produce an acoustic waveform that is propagated into the subject and received by a second one of the transducers along a path that includes the bone and (ii) characteristic determination means for determining a characteristic of the behavior of the waveform along the path; the control module including a microprocessor for controlling motors for causing displacement of the yoke and therefore the transducers over the calcaneus, the module having a control port over which the microprocessor receives control signals for the motors from a master microprocessor.

8. An appliance according to claim 5, wherein a selected one of the transducers employs a vibrating element that is sufficiently small as to cause the selected transducer, if driven by the signal generator, to produce an acoustical output, into the body part, that is substantially like that of a point source.

9. An appliance according to claim 8, wherein the selected transducer employs a resonating element that has a diameter of less than 2 cm.

10. An appliance according to claim 8, wherein the selected transducer employs a resonating element that has a diameter of less than 1 cm.

11. An appliance according to claim 8, wherein each of the transducers employs a resonating element that has a diameter less than 1 cm.

12. An appliance according to claim 8, wherein each of the transducers employs a resonating element that has a diameter less than 0.5 cm.

13. An apparatus for externally determining in a vertebrate subject proximity of an ultrasonic signal path to an edge of a bone disposed within a body part, the apparatus comprising:
   a. first and second transducers wherein each of the transducers employs a vibrating element that is sufficiently small as to cause each transducer, if driven by the signal generator, to produce an acoustic output, into the body part, that is substantially like that of a point source;
   b. a mounting arrangement for mounting the transducers in spaced relationship with respect to the bone;
   c. a signal generator, in communication with the first transducer, for causing the first transducer to produce an acoustic signal, having energy distributed over a frequency range, that is propagated in the subject and received by the second transducer along a first path that includes the bone;
   d. a signal processor, in communication with the second transducer, for determining a measure of the relative proportion of high frequency energy in relation to low frequency energy of the signal received by the second transducer, such proportion being an indication of the proximity of the first path to an edge of the bone.

14. A method for externally determining in a vertebrate subject proximity of an ultrasonic signal path to an edge of a bone disposed within a body part, the method comprising:
   a. providing first and second transducers wherein each of the transducers employs a vibrating element that is sufficiently small as to cause each transducer, if driven by the signal generator, to produce an acoustic output, into the body part, that is substantially like that of a point source;
   b. mounting the transducers in spaced relationship with respect to the bone;
   c. utilizing a signal generator, in communication with the first transducer, for causing the first transducer to produce an acoustic signal, having energy distributed over a frequency range, that is propagated in the subject and received by the second transducer along a first path that includes the bone; and
   d. processing the signal received by the second transducer, so as to determine a measure of the relative proportion of high frequency energy in relation to low frequency energy of the signal received by the second transducer, such proportion being an indication of the proximity of the first path to an edge of the bone.

* * * * *